US011154194B2

(12) United States Patent
Mohanty et al.

(10) Patent No.: US 11,154,194 B2
(45) Date of Patent: Oct. 26, 2021

(54) DEVICE AND METHOD FOR OPTICAL RETINOGRAPHY

(71) Applicant: Nanoscope Technologies, LLC, Arlington, TX (US)

(72) Inventors: Samarendra Kumar Mohanty, Arlington, TX (US); Subrata Batabyal, Arlington, TX (US)

( * ) Notice: Subject to any disclaimer, the term of this patent is extended or adjusted under 35 U.S.C. 154(b) by 0 days.

(21) Appl. No.: 16/179,944

(22) Filed: Nov. 4, 2018

(65) Prior Publication Data
US 2019/0282088 A1 Sep. 19, 2019

Related U.S. Application Data

(60) Provisional application No. 62/581,176, filed on Nov. 3, 2017.

(51) Int. Cl.
A61B 3/12 (2006.01)
A61B 3/10 (2006.01)
A61B 3/00 (2006.01)

(52) U.S. Cl.
CPC .............. A61B 3/12 (2013.01); A61B 3/0008 (2013.01); A61B 3/102 (2013.01); A61B 3/1208 (2013.01)

(58) Field of Classification Search
CPC ....... A61B 3/113; A61B 3/102; A61B 5/0066; A61B 3/14; A61B 5/163; A61B 3/028;
(Continued)

(56) References Cited

U.S. PATENT DOCUMENTS 7,720,526 B1 * 5/2010 Modell .............. G01B 9/02097
600/476
8,041,091 B2 10/2011 Ramos et al.
(Continued)

FOREIGN PATENT DOCUMENTS

WO WO 2016/145367 * 9/2016

OTHER PUBLICATIONS

Wojtkowski "in vivo human retinal imaging by Fourier domain optical coherence tomography" Journal of Biomedical Optics (Year: 2002).*
(Continued)

Primary Examiner — Amy R Weisberg
(74) Attorney, Agent, or Firm — CrossPond Law

(57) ABSTRACT

Principles of the present disclosure are directed to novel methods and devices for focal or global optical stimulation of retina and detecting activity of the retina by collecting and processing the back-scattered optical signal from the retina (Optical RetinoGram). Specifically, the invention provides device and method for quantitatively determining the layer specific activity of retina from the acquired intrinsic back reflected signal by monitoring phase/intensity fluctuations and thereafter employing multifractality algorithm on optical signal for obtaining various multifractal parameters such as width of singularity spectrum, Hurst exponent, fractal dimension, locally connected fractal mapping as well as artificial intelligence based classification for the use of diagnosis of retinal degenerative/ocular disease(s) and asses the progression of diseases or recovery of function due to one or more treatment by therapeutic drugs, devices, protocols.

21 Claims, 14 Drawing Sheets
(13 of 14 Drawing Sheet(s) Filed in Color)

(58) Field of Classification Search
CPC ........... A61B 5/6821; A61B 8/10; A61B 3/12; A61B 3/1208; A61B 3/0008
See application file for complete search history.

(56) References Cited

U.S. PATENT DOCUMENTS

| | | | |
|---|---|---|---|
| 8,690,330 | B2 | 4/2014 | Hacker et al. |
| 9,750,406 | B2 | 9/2017 | Ramo et al. |
| 10,219,693 | B2* | 3/2019 | Mikaelian ............... A61B 3/024 |
| 2015/0371383 | A1 | 12/2015 | Chabrier et al. |
| 2016/0252340 | A1* | 9/2016 | Hollenbeck ........ G01B 9/02091 356/479 |
| 2018/0070814 | A1* | 3/2018 | Mikaelian ............... A61B 3/024 |
| 2018/0206716 | A1* | 7/2018 | Chong ...................... A61B 3/12 |

OTHER PUBLICATIONS

B. E. Bouma aGJT. Handbook of Optical Coherence Tomography. New York: Informa Healthcare; 2001.

Adler D C, Huber R, Fujimoto J G. Phase-sensitive optical coherence tomography at up to 370,000 lines per second using buffered Fourier domain mode-locked lasers. Opt Lett. 2007; 32(6):626-8.

Akkin T, Dave D P, Milner T E, Rylander Iii H G. Detection of neural activity using phase-sensitive optical low-coherence reflectometry. Opt Express. 2004; 12(11):2377-86.

Barteselli G, Gomez M L, Doede A L, Chhablani J, Gutstein W, Bartsch D U, et al. Visual function assessment in simulated real-life situations in patients with age-related macular degeneration compared to normal subjects. Eye (Lond). 2014; 28(10):1231-8.

Batabyal S, Satpathy S, Bui L, Kim Y T, Mohanty S, Bachoo R, et al. Label-free optical detection of action potential in mammalian neurons. Biomedical optics express. 2017; 8(8):3700-13.

Biarnes M, Mones J, Alonso J, Arias L. Update on geographic atrophy in age-related macular degeneration. Optom Vis Sci 2011; 88(7):881-9.

Boyden E S, Zhang F, Bamberg E, Nagel G, Deisseroth K. Millisecond-timescale, genetically targeted optical control of neural activity. Nat Neurosci. 2005; 8(9):1263-8.

Brezinski M. Optical Coherence Tomography: Principles and Applications. London: Academic Press; 2006.

Busskamp V, Picaud S, Sahel J A, Roska B. Optogenetic therapy for retinitis pigmentosa. Gene Ther. 2012; 19 (2):169-75.

Chader G J. Animal models in research on retinal degenerations: past progress and future hope. Vision Res. 2002; 42 (4):393-9.

Chiu S J, Izatt J A, O'Connell R V, Winter K P, Toth C A, Farsiu S. Validated automatic segmentation of AMD pathology including drusen and geographic atrophy in SD-OCT images. Invest Ophthalmol Vis Sci. 2012; 53(1):53-61.

Choma M A, Ellerbee A K, Yang C, Creazzo T L, Izatt J A. Spectral-domain phase microscopy. Opt Lett. 2005; 30 (10):1162-4.

Chong E W, Wong T Y, Kreis A J, Simpson J A, Guymer R H. Dietary antioxidants and primary prevention of age related macular degeneration: systematic review and meta-analysis. BMJ. 2007; 335(7623):755.

Chowers I, Banin E, Merin S, Cooper M, Granot E. Long-term assessment of combined vitamin A and E treatment for the prevention of retinal degeneration in abetalipoproteinaemia and hypobetalipoproteinaemia patients. Eye (Lond). 2001; 15(Pt 4):525-30.

Curcio C A, Medeiros N E, Millican C L. Photoreceptor loss in age-related macular degeneration. Invest Ophthalmol Vis Sci. 1996; 37(7):1236-49.

Daiger S P, Bowne S J, Sullivan L S. Perspective on genes and mutations causing retinitis pigmentosa. Arch Opthalmol. 2007; 125(2):151-8.

Fercher A F, Drexler W, Hitzenberger C K, Lasser T. Optical coherence tomography—principles and applications. Reports on Progress in Physics. 2003; 66(2):239.

Flannery J G, Farber D B, Bird A C, Bok D. Degenerative changes in a retina affected with autosomal dominant retinitis pigmentosa. Invest Ophthalmol Vis Sci. 1989; 30(2):191-211.

Grover S, Fishman G A, Anderson R J, Alexander K R, Derlacki D J. Rate of visual field loss in retinitis pigmentosa. Opthalmology 1997; 104(3):460-5.

Grunwald J E, Pistilli M, Ying G S, Maguire M G, Daniel E, Martin D F. Growth of Geographic Atrophy in the Comparison of Age-related Macular Degeneration Treatments Trials. Ophthalmology. 2014.

Gu L, Mohanty S K. Targeted microinjection into cells and retina using optoporation. J Biomed Opt. 2011; 16 (12):128003-6.

Hartong D T, Berson E L, Dryja T P. Retinitis pigmentosa. Lancet. 2006; 368(9549):1795-809.

Hausler G, Lindner M W. "Coherence Radar" and "Spectral Radar"—New Tools for Dermatological Diagnosis. Journal of Biomedical Optics. 1998; 3(1):21-31.

Hee M R, Izatt J A, Swanson E A, Huang D, Schuman J S, Lin C P, et al. Optical coherence tomography of the human retina. Arch Ophthalmol. 1995; 113(3):325-32.

Hee M R, Puliafito C A, Wong C, Duker J S, Reichel E, Schuman J S, et al. Optical coherence tomography of macular holes. Ophthalmology. 1995; 102(5):748-56.

Jia Y, Morrison J C, Tokayer J, Tan O, Lombardi L, Baumann B, et al. Quantitative OCT angiography of optic nerve head blood flow. Biomedical optics express. 2012; 3(12):3127-37.

Joo C, Kim K H, de Boer J F. Spectral-domain optical coherence phase and multiphoton microscopy. Opt Lett. 2007; 32(6):623-5.

Kim B J, Braun T A, Wordinger R J, Clark A F. Progressive morphological changes and impaired retinal function associated with temporal regulation of gene expression after retinal ischemia/reperfusion injury in mice. Mol Neurodegen. 2013; 8:21.

Klezovitch O, Risk M, Coleman I, Lucas J M, Null M, True L D, et al. A causal role for ERG in neoplastic transformation of prostate epithelium. Proc Natl Acad Sci USA. 2008; 105(6):2105-10.

Li Z Y, Jacobson S G, Milam A H. Autosomal dominant retinitis pigmentosa caused by the threonine-17-methionine rhodopsin mutation: retinal histopathology and immunocytochemistry. Exp Eye Res. 1994; 58(4):397-408.

Mezer E, Babul-Hirji R, Wise R, Chipman M, DaSilva L, Rowell M, et al. Attitudes Regarding Predictive Testing for Retinitis Pigmentosa. Ophthalmic Genetics. 2007; 28(1):9-15.

Miller G. Shining New Light on Neural Circuits. Science. 2006; 314(5806):1674-6.

Mohanty S K, Reinscheid R K, Liu X, Okamura N, Krasieva T B, Berns M W. In-Depth Activation of Channelrhodopsin 2-Sensitized Excitable Cells with High Spatial Resolution Using Two-Photon Excitation with a Near-Infrared Laser Microbeam. Biophys J. 2008; 95(8):3916-26.

Mukhopadhyay S, Das N K, Kurmi I, Pradhan A, Ghosh N, Panigrahi P K. Tissue multifractality and hidden Markov model based integrated framework for optimum precancer detection. J Biomed Opt. 2017; 22(10):1-8.

Nagel G, Szellas T, Huhn W, Kateriya S, Adeishvili N, Berthold P, et al. Channelrhodopsin-2, a directly light-gated cation-selective membrane channel. Proc Nat Acad Sci. 2003; 100(24):13940-5.

Palmowski A M, Sutter E E, Bearse M A, Jr., Fung W. Mapping of retinal function in diabetic retinopathy using the multifocal electroretinogram. Invest Ophthalmol Vis Sci. 1997; 38(12):2586-96.

Sarunic M V, Weinberg S, Izatt J A. Full-field swept-source phase microscopy. Opt Lett. 2006; 31(10):1462-4.

Shimada Y, Li Y, Bearse M A, Jr., Sutter E E, Fung W. Assessment of early retinal changes in diabetes using a new multifocal ERG protocol. Br J Ophthalmol. 2001; 85(4):414-9.

Sugawara T, Hagiwara A, Hiramatsu A, Ogata K, Mitamura Y, Yamamoto S. Relationship between peripheral visual field loss and vision-related quality of life in patients with retinitis pigmentosa. Eye (Lond). 2010; 24(4):535-9.

(56) References Cited

OTHER PUBLICATIONS

Sunness J S, Margalit E, Srikumaran D, Applegate C A, Tian Y, Perry D, et al. The long-term natural history of geographic atrophy from age-related macular degeneration: enlargement of atrophy and implications for interventional clinical trials. Ophthalmology. 2007; 114(2):271-7.

Swanson E A, Izatt J A, Hee M R, Huang D, Lin C P, Schuman J S, et al. In vivo retinal imaging by optical coherence tomography. Opt Lett. 1993; 18(21):1864-6.

Terao T, Nakayama T, Aoki H. Multifractality of the quantum Hall wave functions in higher Landau levels. Phys Rev B Condens Matter. 1996; 54(15):10350-3.

Tomlins P H, Wang R K. Theory, developments and applications of optical coherence tomography. Journal of Physics D: Applied Physics. 2005; 38(15):2519.

Waheed N K, Moult E M, Fujimoto J G, Rosenfeld P J. Optical Coherence Tomography Angiography of Dry Age-Related Macular Degeneration. Dev Ophthalmol. 2016; 56:91-100.

Wallsh J, Gallemore R. Optical coherence tomography difference maps and average macular volume for geographic atrophy. Retin Cases Brief Rep. 2015; 9(1):88-91.

Wang R K, Nuttall A L. Phase-sensitive optical coherence tomography imaging of the tissue motion within the organ of Corti at a subnanometer scale: a preliminary study. Journal of Biomedical Optics. 2010; 15(5):056005-9.

Wildberger H, Niemeyer G, Junghardt A. Multifocal electroretinogram (mfERG) in a family with occult macular dystrophy(OMD). Klin Monbl Augenheilkd. 2003; 220(3):111-5.

Witkin A J, Ko T H, Fujimoto J G, Chan A, Drexler W, Schuman J S, et al. Ultra-high resolution optical coherence tomography assessment of photoreceptors in retinitis pigmentosa and related diseases. Am J Ophthalmol. 2006; 142 (6):945-52.

Wojtkowski M, Srinivasan V, Fujimoto J G, Ko T, Schuman J S, Kowalczyk A, et al. Three-dimensional retinal imaging with high-speed ultrahigh-resolution optical coherence tomography. Ophthalmology. 2005; 112(10):1734-46.

Wu Z, Ayton L N, Luu C D, Guymer R H. Microperimetry of nascent geographic atrophy in age-related macular degeneration. Invest Ophthalmol Vis Sci. 2015; 56(1):115-21.

Yeh Y J. Black A J, Akkin T. Spectral-domain low-coherence interferometry for phase-sensitive measurement of Faraday rotation at multiple depths. Appi Opt. 2013; 52(29):7165-70.

Zhang F, Aravanis A M; Adamantidis A, de Lecea L, Deisseroth K. Circuit-breakers: optical technologies for probing neural signals and systems. Nat Rev Neurosci. 2007; 8(8):577-81.

Zhang F, Wang L P, Boyden E S, Deisseroth K ChannelModopsin-2 and optical control of excitable cells. Nat Methods. 2006; 3(10):785-92.

Zhang F, Wang L-P, Brauner M, Liewald J F, Kay K, Watzke N, et al. Multimodal fast optical interrogation of neural circuitry. Nature. 2007; 446(7136):633-9.

Zhao Y, Chen Z, Saxer C, Xiang S, de Boer J F, Nelson J S. Phase-resolved optical coherence tomography and optical Doppler tomography for imaging blood flow in human skin with fast scanning speed and high velocity sensitivity. Optics letters. 2000; 25(2):114-6.

\* cited by examiner

Figure 1: Flow Chart for imaging and analysis

Figure 10A
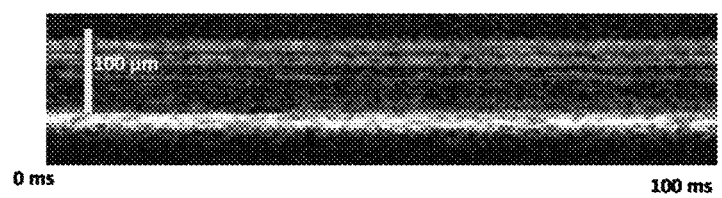
Figure 10 B
Figure 10C
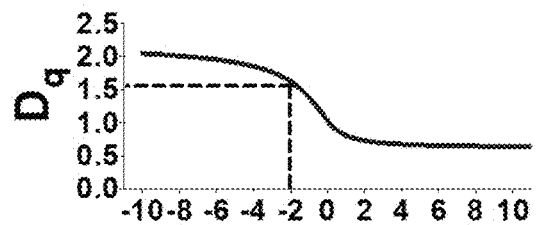
Figure 10D
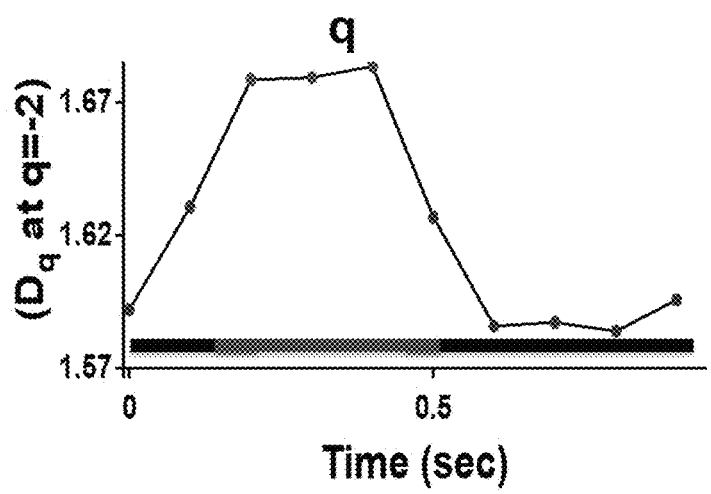
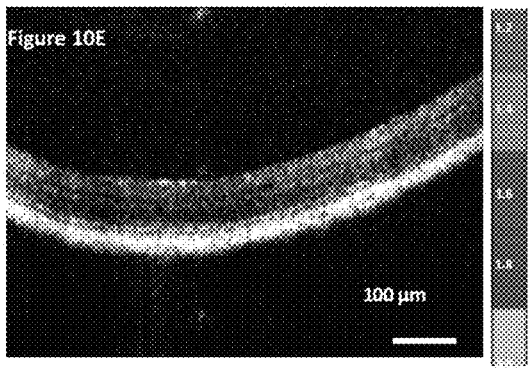
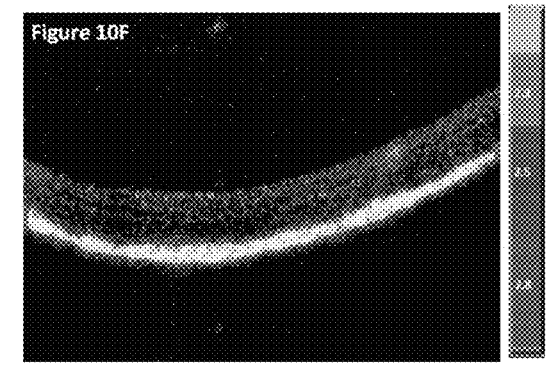

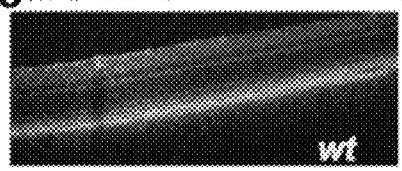
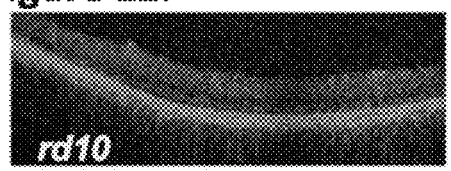
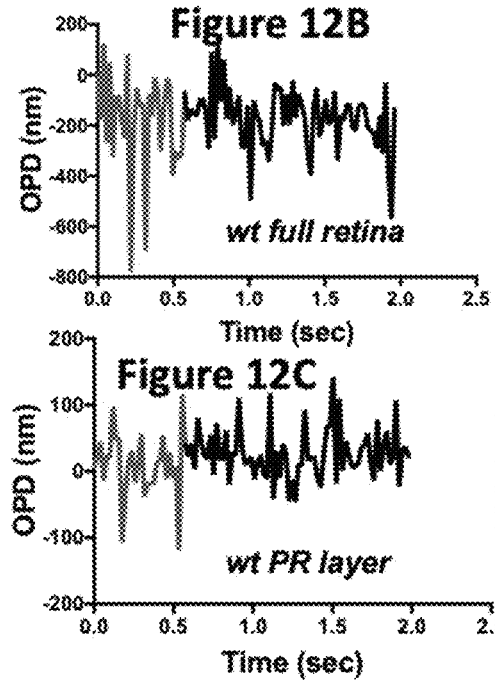
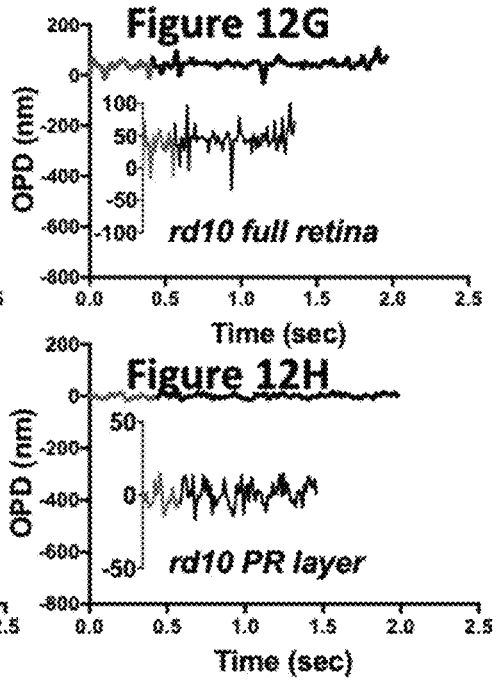
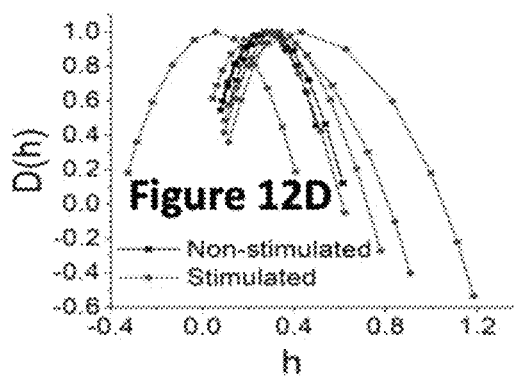
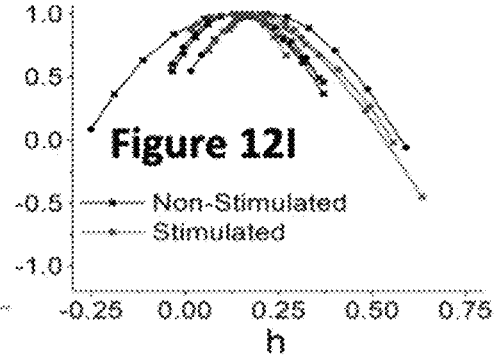
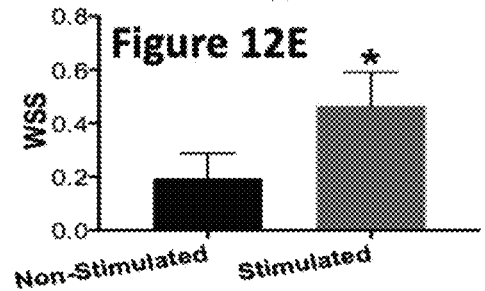
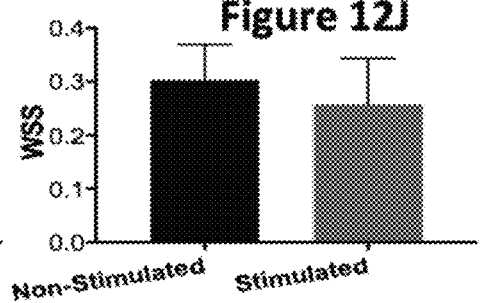

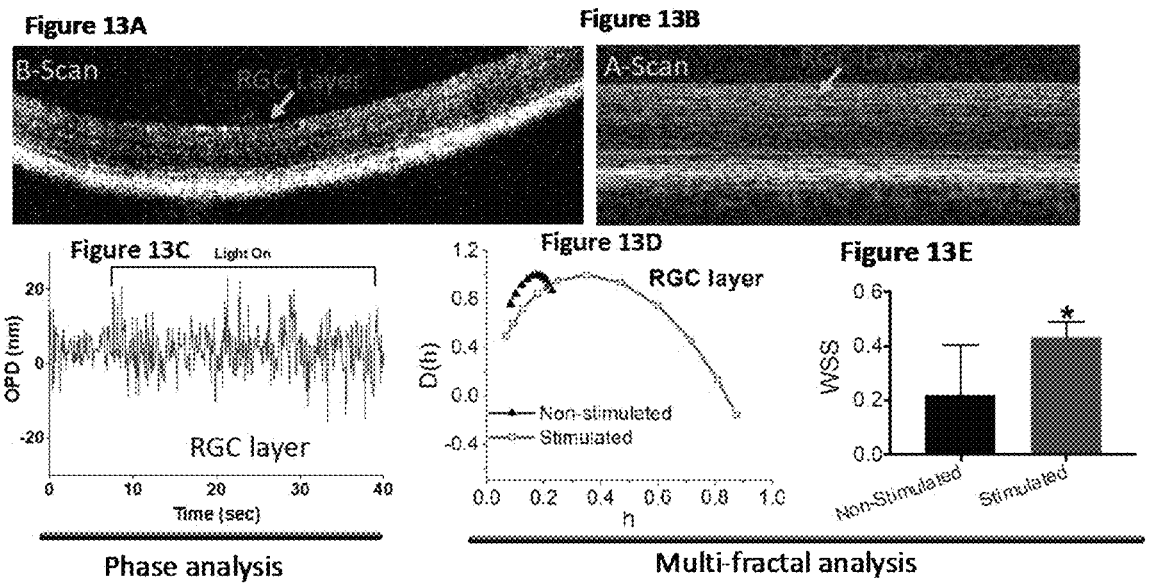

DEVICE AND METHOD FOR OPTICAL RETINOGRAPHY

CROSS-REFERENCE

This application claims the benefit of U.S. provisional application No. 62/581,176 filed Nov. 3, 2017, which application is incorporated herein by reference.

Some references, which may include publications, patents, and patent applications, are cited and discussed in the description of this invention. The citation and/or discussion of such references is provided merely to clarify the description of the present invention and is not an admission that any such reference is "prior art" to the invention described herein. All references cited and discussed in this specification are incorporated herein by reference in their entireties and to the same extent as if each reference were individually incorporated by reference.

STATEMENT REGARDING FEDERALLY SPONSORED RESEARCH OR DEVELOPMENT

This invention was made with private funding by NanoScope Technologies, LLC. The government has no rights in the invention.

FIELD OF THE INVENTION

The present disclosure relates to devices and methods for detecting retinal activity in vivo using intrinsic optical information from interferometric scans.

The present disclosure is directed to a novel method and systems for focal or global optical stimulation of retina and detecting activity of the retina by collecting and processing the back-scattered optical signal from the retina.

The present disclosure is further directed to quantitatively determine layer specific activity of retina from the acquired intrinsic back reflected signal and obtaining the temporal change of optical properties (such as phase, scattering, polarization).

Another embodiment of the present disclosure provides a method for the diagnosis of retinal disease(s) in a mammalian subject eye, the method comprising: obtaining optical interferometric scan signal from a region of interest in the retina; and quantifying the layer-specific activity in the region upon light stimulation; and asses the progression of diseases or recovery of function due to therapeutic treatment.

Another embodiment of the present invention, the detection of retinal function and disease state can be estimated using spatial variation of refractive index in tissues exhibiting multifractality and disease progression can be monitored by distinct changes in multifractal parameters (generalized exponent and width of the singularity spectrum, WSS). Multifractality of nano/micro-structural changes in 2D-spatial distribution of reflected light intensity is used to generate locally-connected fractal dimension ($D_{LC}$) which uses pixel mass from concentrically placed sampling units.

In another aspect of the invention, the retinal function and early disease indication can be detected and quantified using multifractality in time-varying reflected light intensity from different layers (measured by interferometric scan). Multifractality in temporal fluctuations in optical path difference (measured by phase scan interferometry) provides information of retinal functional state. The multifractal parameters provide a distinct measure of how much the local regularity of the interferometric signal varies in time.

Another embodiment of the present disclosure provides the deployment of artificial intelligence and convoluted neural network in analysis locally connected multifractal map and multifractal parameters for deep learning of different diseases state and provide classifier output of early indicative of different ocular disease state.

According to another aspect of the invention, the disclosed invention provides method for the use of the interferometric method to measure activity of retinal cells expressing endogenous opsins for vision restoration and other application.

BACKGROUND OF THE INVENTION

Measurement of neural activities in-vivo is essential for assessment of neurological disorders. Several electrical, magnetic and electromagnetic methods including functional optical imaging is used for detection of neural activity of retina and central nervous system. In case of loss of vision by retinal degenerative diseases such as dry-AMD) (1-3) and Retinitis Pigmentosa (RP) (4, 5), the photoreceptors are degenerated (6, 7), leading to loss of light induced activity of the retina. The current functional diagnostics of retina rely on psychophysical and electrical measurements (8-11), which have limitations in assessing local function of specific retinal layers, and thus may miss early onset of the disease progression. In case some ocular disease such as of glaucoma, detection of early stage indication remains elusive due to technical challenges as the primary methods of assessment of eye health (conventional optical coherence tomography (OCT)(12-15), light microscopy, measurement of IOP) cannot provide local functional measures in retina. These methods are only able to detect the occurrence of glaucoma when it has already advanced. Further, these modalities have limitation in measuring eye diseases due to slowly advancing nature of the disease and lack of common reference standard. Electroretinography (ERG) is used to detect abnormal function of the retina due to loss of photoreceptors or other retinal layers. ERG recording requires placement of electrode(s) on the cornea to measure the electrical responses of the retina in response to light.

Though there are patent literature (16-19) of determining ocular function, none of them have utilized combination phase/intensity of OCT signal integrated with multifractality (20) analysis to determine the retinal function and provide clinically meaningful parameters for detection of ocular diseases at early stage. For example, U.S. Pat. No. 9,750,406 describes the optical quality of a patient's eye based on one or more retinal images thereof or based on information relating to retinal images corresponding to an eye having an anterior segment and intraocular means that are healthy. Another relevant U.S. Pat. No. 8,041,091 describe the use of image analysis system allows users to import digital color fundus images over time and group such images for processing so as to generate analyses. The other patents such as (i) US20150371383A1 describes retinal diagnostic/treatment systems based on mark-up a mosaic image in order to do a treatment plain (ii) WO2009089509A1: Disclosed is a method for detecting a physiological in neurons using fast intrinsic optical signals created by a response to visible light as measured by near infrared light; (iii) U.S. Pat. No. 7,118,217: describes the use of reflectance of near infrared light from the retina of human subjects in response to visual activation of the retina by a pattern stimulus.

While use of calcium/voltage sensitive dyes or genetically encoded $Ca^{2+}$ and voltage indicators (21-23) for functional optical imaging is valuable for in-vitro or animal studies, it has limitations for clinical use due to requirement of injection of exogenous labeling, which can be toxic.

Low-coherence optical interferometry based back-scattered intensity mapping, also known as Optical Coherence Tomography (OCT)(14, 24, 25), is a non-invasive, label-free optical imaging technique that uses low coherence light to produce depth-resolved reflectance imaging of samples. OCT imaging allows three-dimensional (3D) structural visualization with micrometer resolution.

OCT has gained wide acceptance as a promising in-vivo imaging tool in ophthalmology practices (26-30). Time-Domain (TD) OCT utilizes axial scanning of reference arm to generate the depth profile of the sample. Fourier-domain (FD) employment of OCT enable depth-profiling without scanning of the reference mirror, thus allowing high speed 3D imaging of retinal layers. In FD-OCT, the interference signal is detected by a linear array of CCDs and then Fourier transformed to obtain the structural image from the amplitude of the Fourier transformed signal.

General uses of OCT include structural depth resolved 3D imaging of various specimen, including retina, blood vasculature etc. Previously described methods have employed OCT based interferometric techniques to measure scattering changes in the retinal layers or blood vessels (31, 32). However, none of these methods have disclosed the detection of layer specific activities based on phase analysis of interferometric recording in presence of targeted (focal) or global stimulation.

The synchronous focal or global stimulation with label-free detection of retinal activity can be very useful to understand the state of the disease(s) as well as the effect of therapeutic treatment(s).

Currently, there are no non-contact optical measurement techniques to detect functional changes along with superior structural mapping in retinal layers in-vivo in eye for early diagnosis of ocular diseases such as Glaucoma or AMD. There is a need in the art for improved methods and devices for non-invasive detection of retinal activities for a variety of applications including but not limited to the diagnosis and treatment of various ocular diseases.

SUMMARY OF THE INVENTION

The current functional diagnostics of retina rely on psychophysical and electrical measurements, which have limitations in assessing local function of specific retinal layers, and thus may miss early onset of the disease progression. To overcome the challenges, the inventor has created a device and method with different modalities for synchronous focal or global retinal stimulation along with phase-measurements by optical interferometry to detect retinal activity in order to understand the disease state as well as effect of therapeutic treatment on the progression of the disease. The developed optical interferometry (amplitude/phase-sensitive interferogram) based Focal detection of Focally stimulated Optical RetinoGram (ffORG) coupled with multifractal analysis (33, 34) (20) enables measurement of sub-nanometer optical path-length (OPL) changes during functional activation in photo-transducing circuitry of the retina. More importantly, findings show that the temporal fluctuations of OPL and spatial variation of reflected intensity exhibit multifractality (MF), which changes during light activation and thus provide useful medical insight of functioning of visual circuitry. The ffORG studies coupled with in-depth multifractal analysis differentiated retinal activities in wild type mice with photoreceptors degeneration, and glaucoma mice model having ganglion cell dysfunction.

One embodiment of the disclosed invention is to obtain Optical RetinoGram (ORG) for in-vivo label free detection of retinal layer activity under different conditions by using a method comprising of optical low coherence reflectometry scanning on retinal layer. In presence or absence of stimulation (focal (ffORG), patterned or global (fORG)), specific activity in the retinal layer can be quantitatively obtained from the acquired optical interferogram (temporal phase modulation) by monitoring the change of optical path length variation with time.

In another embodiment, the present disclosure provides a method for the diagnosis of retinal disease in a subject eye. The method comprising of point scan (A-scan) on specific position of the retina and obtain optical signal under stimulation and asses the disease state and its progression with time.

Another embodiment of the disclosed invention provides ORG method to screen or optimize one or more therapeutic drugs, devices, protocols, and/or monitor recovery of retinal function due to therapeutic treatment.

In yet another embodiment, the disclosed invention provides method for the use of ORG scanning device to monitor the functional recovery of degenerated retina after delivery gene of interest (e.g. Opsin gene) into targeted retinal area (s).

In yet another embodiment, the disclosed invention provides a non-invasive approach to remotely detect targeted layer-specific retinal activities in the degenerated retinal regions in dry-AMD patients.

In another embodiment, the disclosed invention provides a way to generate multifractality map associated with of nanostructural changes in retina and trabecular meshwork. 2D-spatial distribution of reflected light intensity (measured by B-scan) is generated from Locally-connected fractal dimension ($D_{LC}$) analysis which uses pixel mass from concentrically placed sampling units, using the connected set at each pixel to produce a distribution of local variation in complexity. The multifractality variations (in different retinal layers and within the same layer and in trabecular meshwork serves as the marker for the nanostructural variations, which is associated with ocular function and thus help to identify early disease indication and structural changes associated disease progression.

In yet another embodiment, the disclosed invention provides a way of assessing retinal function and disease state by my monitoring multifractality in temporal fluctuations in optical path difference (measured by PS-OCT) upon photo-stimulation. Multifractality in time-varying reflected light intensity from different layers (measured by A-scans) is used to generate fractal parameters such as Generalized dimension ($D_q$) and width of singularity spectrum (WSS) which is directly related to retinal functional state. The spatial variation of refractive index in tissues exhibits multifractality and disease progression is exhibited by distinct changes in multifractal parameters (generalized dimension and width of the singularity spectrum, WSS). Our innovation includes in-depth multifractal analysis of the spatial and temporal-varying optical phase scan data as follows.

In another aspect of invention includes the use of the ffORG measurements (Phase/OPD fluctuation amplitude, width of singularity spectrum, fractal dimension, Hurst exponent etc.) to feed into convoluted neural network as training data set for developing artificial intelligence based diagnostic tool which can be used in clinical setting.

In a broader aspect, the disclosure provides methods for use in diagnosis of retinal diseases and monitor efficacy and progress of treatment by physical, chemical, genetic and other methods.

It is contemplated that any embodiment of a method or composition described herein can be implemented with respect to any other method or composition described herein.

Details associated with the embodiments described above and others are described below.

Other objects, features and advantages of the present invention will become apparent from the following detailed description. It should be understood, however, that the detailed description and the specific examples, while indicating specific embodiments of the invention, are given by way of illustration only, since various changes and modifications within the spirit and scope of the invention will become apparent to those skilled in the art from this detailed description.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

The following drawings illustrate by way of example and not limitation. For the sake of brevity and clarity, every feature of a given structure is not always labeled in every figure in which that structure appears. The following drawings form part of the present specification and are included to further demonstrate certain aspects of the present invention. The invention may be better understood by reference to one or more of these drawings in combination with the detailed description of the specification embodiments presented herein.

FIG. 4B represents the measured OPD signal from the composite of retinal with time.

FIG. 10A shows the A-scan OCT image of retina without light stimulation. FIG. 10B shows the A-scan OCT image of retina with focal (spot: ~10 µm) light stimulation. FIG. 10C shows the plot of $D_q$ versus q. FIG. 10D shows the increase in D (q=−2) upon focused stimulation (red bar). Multifractality in time-varying reflected light intensity from retinal layers (A-scan OCT) changes upon light stimulation. FIG. 10E shows the reflected light intensity OCT image of retina. FIG. 10F shows the locally-connected multifractality levels of nanostructural variations in the reflected light intensity OCT image. Color map: Locally-connected fractal dimension.

FIG. 12A shows the cross-sectional view of the wild type retina. FIG. 12B and FIG. 12C show the FORG response measured with the visual stimulation light on (red) and off (black) at a point from the whole retina, and photoreceptor layer respectively. FIG. 12D shows the multifractal spectra. FIG. 12E shows the quantitative comparison of WSS for stimulated vs. non-stimulated retina. *$p<0.05$. FIG. 12F shows the cross-sectional view of rd10 retina. Axially-averaged (FIG. 12G) and layer-specific (FIG. 12H) retinal FFORG response from rd10 mice measured with the visual stimulation light on (red) and off (black). Insets in FIG. 12G & FIG. 12H show Y-scale zoomed temporal change in OPD. FIG. 12I and FIG. 12J respectively show the multifractal spectrum and WSS with and without stimulation.

FIG. 13A and FIG. 13B show the B-scan and A-scan OCT image of retina respectively. FIG. 13C shows the change in OPD fluctuation upon photo-stimulation. FIG. 13D shows the Multifractal Singularity spectrum (Dh vs h) derived from OPD fluctuations in RGC layer. FIG. 13E shows the Quantitative comparison of width of singularity spectrum (WSS) in RGC layer with and without light. *$p<0.05$.

Figure 1:
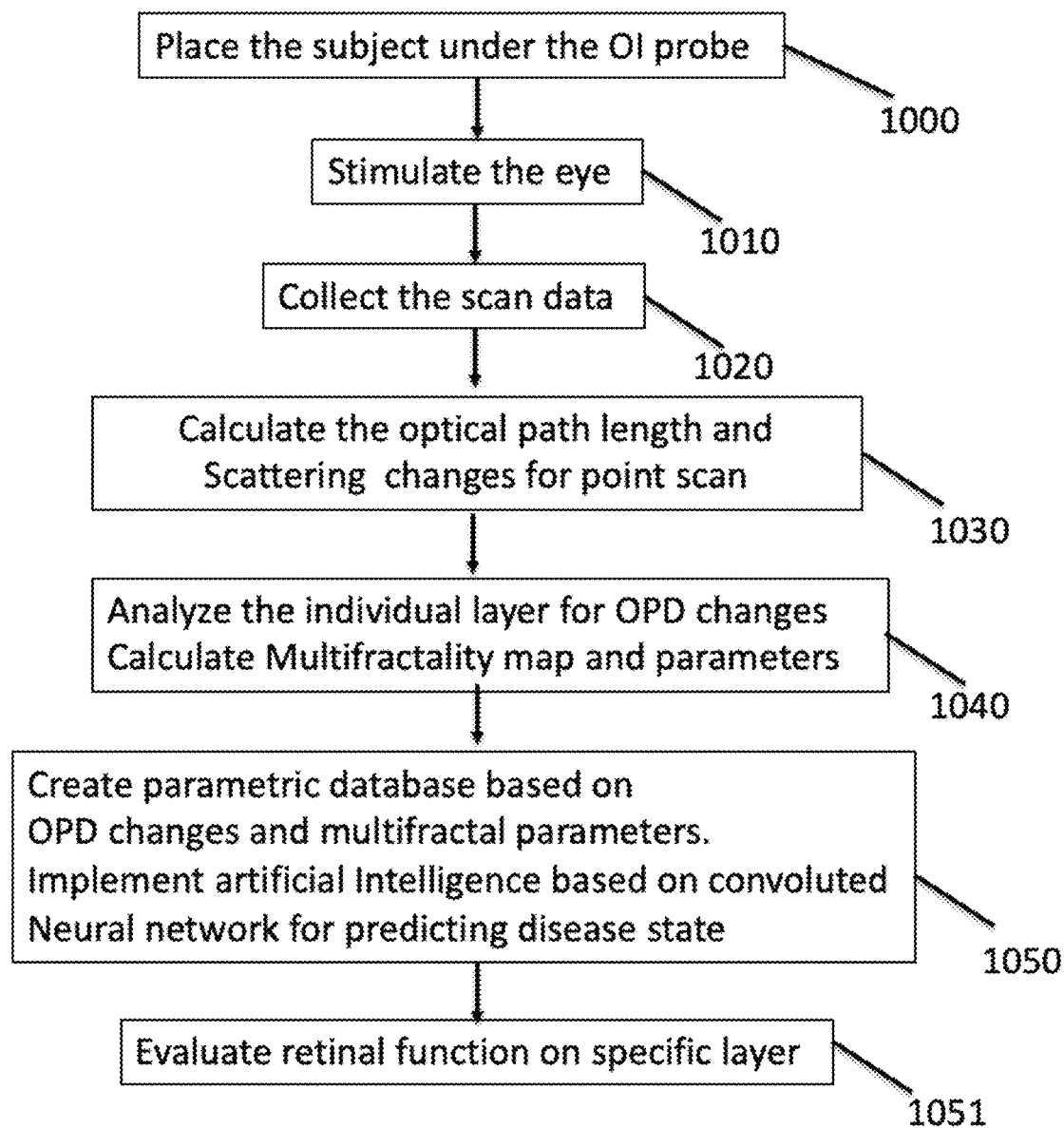
FIG. 1 depicts Flow Chart for interferometry based retinal scanning and analysis for detecting layer specific activity.

While the device and method of the present application is susceptible to various modifications and alternative forms, specific embodiments thereof have been shown by way of example in the drawings and are herein described in detail. It should be understood, however, that the description herein of specific embodiments is not intended to limit the application to the particular embodiment disclosed, but on the contrary, the intention is to cover all modifications, equivalents, and alternatives falling within the spirit and scope of the process of the present application as defined by the appended claims.

DETAILED DESCRIPTION OF THE INVENTION

Illustrative embodiments of the preferred embodiment are described below. In the interest of clarity, not all features of an actual implementation are described in this specification. It will of course be appreciated that in the development of any such actual embodiment, numerous implementation-specific decisions must be made to achieve the developer's specific goals, such as compliance with system-related and business-related constraints, which will vary from one implementation to another. Moreover, it will be appreciated that such a development effort might be complex and time-consuming but would nevertheless be a routine undertaking for those of ordinary skill in the art having the benefit of this disclosure.

In the specification, reference may be made to the spatial relationships between various components and to the spatial orientation of various aspects of components as the devices are depicted in the attached drawings. However, as will be recognized by those skilled in the art after a complete reading of the present application, the devices, members, apparatuses, etc. described herein may be positioned in any desired orientation. Thus, the use of terms to describe a spatial relationship between various components or to describe the spatial orientation of aspects of such components should be understood to describe a relative relationship between the components or a spatial orientation of aspects of such components, respectively, as the device described herein may be oriented in any desired direction.

The device and method in accordance with the present application overcomes one or more of the above-discussed problems commonly associated with traditional approaches discussed above. In particular, the present invention provides new methods, devices and systems for functional optical retinography (fORG) and focal functional optical retinography (ffORG). Generally, fORG/ffORG may comprise a non-invasive, non-contact method for determining a functional state of target mainly retina. In some examples, fORG/ffORG may be used for determining the disease state (such as retinal disorders) and progression of diseases with time. In other use, the method may be used to evaluate the efficacy and potency of therapeutic drug molecules such as for retinal gene therapy.

Phase sensitive Fourier domain optical interferometry (PSFD-OI) is a technique based on the principles of low-coherence interferometry that can detect displacements of the order of sub nanometer by analyzing the phase changes of the Fourier transformed signal in the measured spectral interferrogram (35-37). Current methods rely on electrical recording that requires electrode to be in contact to the eye and lack specificity in the recorded electrical signal. The innovativeness includes development of an integrated focal optical stimulation and detection system combined with fast optical information processing capable of resolving layer specific retinal activity using intrinsic optical signals having important diagnostic applications in ophthalmology. Our fORG/ffORG system (FIG. 2, FIG. 6, FIG. 7, FIG. 8, FIG. 9) utilizes optical interferometry of back-scattered light for label-free monitoring of functional state of retina and response to focal visual stimulation.

The ORG signal (i.e. change in optical path length) is a convoluted change in physical path length and refractive index in retina during visual stimulation. FFORG allows diagnosis of disease state in targeted areas of retina based on its response to focal stimulation. The ffORG system enables us to capture 3D near-infrared image of backscattered light, thereby achieving precise signal localization and minimizing additional undesired photo stimulation. This depth-resolved functional imaging enables resolving layer specific retinal activity for monitoring progression of photoreceptor degeneration and/or retinal-circuitry dysfunction. FFORG provides accurate assessment of retinal function by testing retinal sensitivity at specific 3D location, that can be selected based on treatment. The present disclosure provides methods and systems for detecting retinal function from a specific position by axial A scan (fORG).

Generally, fORG/ffORG uses any methodology of low coherence optical interferometry, as known in the art. fORG/ffORG provide a method of extracting a full set of optical properties from the back reflected intrinsic optical signal and extracting optical information (phase and scattering) from the optical interference data set. The optical path-length change during optical stimulation can be measured from the phase data encoded in a specified frequency or frequency range obtained from the FFT analysis of the interferogram. In some examples, the same or single A-scan generated from optical interferometry scans may be used for calculations. For example, the target may be a human/murine retina or any other m, where the activity of retina under different visual cue be determined using the ORG system. A schematic for determining the change of functional retinal activity under visual stimulation in given in FIG. 1.

Figure 2:
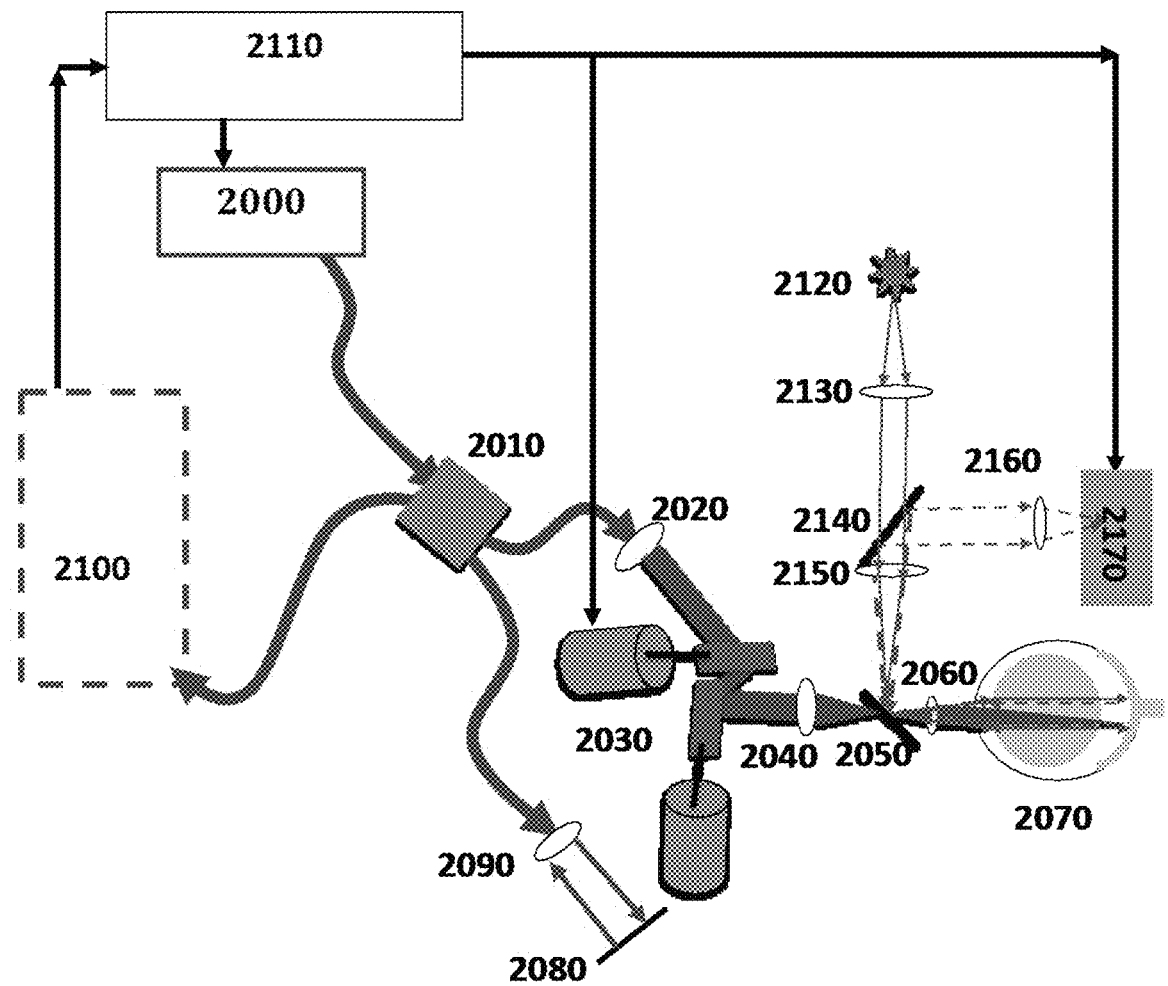
FIG. 2. Phase Sensitive Fourier Domain Optical Interferometry (PS-FD 01) integrated with funduscopic imaging for functional activity monitoring of retina. 2000: low coherence source (SLD); 2010: Fiber coupler; 2020: collimating lens; 2030: X-Y scanning mirror; 2040: Lens 2050: Dichroic mirror, 2060: Lens 2070: Subject eye; 2080: Reference arm mirror; 2090: Collimating lens; 2100: Spectrometer; 2110: Computer, Controller and Display; 2120: Light source; 2130: Condensing lens; 2140: Beam Splitter; 2150: Lens; 2160: Lens; 2170: Camera

Spectral domain implementation of the low coherence interferometry is capable collecting and processing phase information contained in the optical signals. Using PSFD-OI, it is shown to be possible to measure sub-nanometer motion (38). In the PSFD-OI, reference mirror is stationary and the interference signal between the reflected intensities from the reference mirror and the sample microstructures is detected with a spectrometer as a function of wavelength. The detected signal (as a function of wavelength) is then Fourier transformed to obtain intensity profile as a function of depth. Optical scans the whole depth of the sample without any mechanical scanning, which leads to higher phase stability. The schematic diagram of the ORG system is shown in FIG. 2. It uses a broadband super luminescent diode (SLD, central wavelength: 860 nm and bandwidth: ~150 nm, which leads to an axial resolution of ~2 µm in air). The high axial resolution enables in-vivo detection of visual stimulation induced nano-changes of specific retinal layers. The light from the SLD is connected 2×2 coupler as shown in the FIG. 2. One of the outputs of the coupler goes to a reference arm and the other goes to the sample arm to the eye. In this example, sample beam power of ~800 µW was used. The sample arm consisted of a XY scanner and objective lens (the objective lens NA is 0.12). The reference arm consisted of a collimator, which collimates the light from the fiber and a lens that focuses the light on to a mirror. The reflected light from the reference arm and the sample arm go back to the 2×2 coupler and to the connected to the spectrometer. The spectrometer consists of another collimator that collimates the light emanating from the fiber, followed by a transmission grating to spectrally spread the signal. A lens is used to focus the dispersed signal to a line-scanning camera (1024 pixels).

Figure 3A:
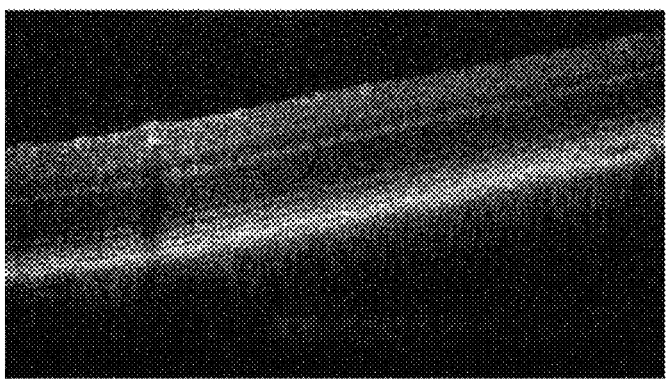
FIG. 3A shows the Cross-sectional view of the retina of a wild type mouse in-vivo and FIG. 3B shows the point scan (A-scan) image for optical detection. The different retinal layers are visible.
Figure 3B:
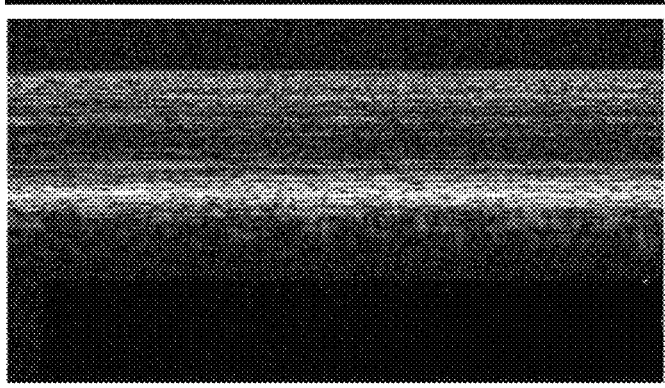
Figure 3C:
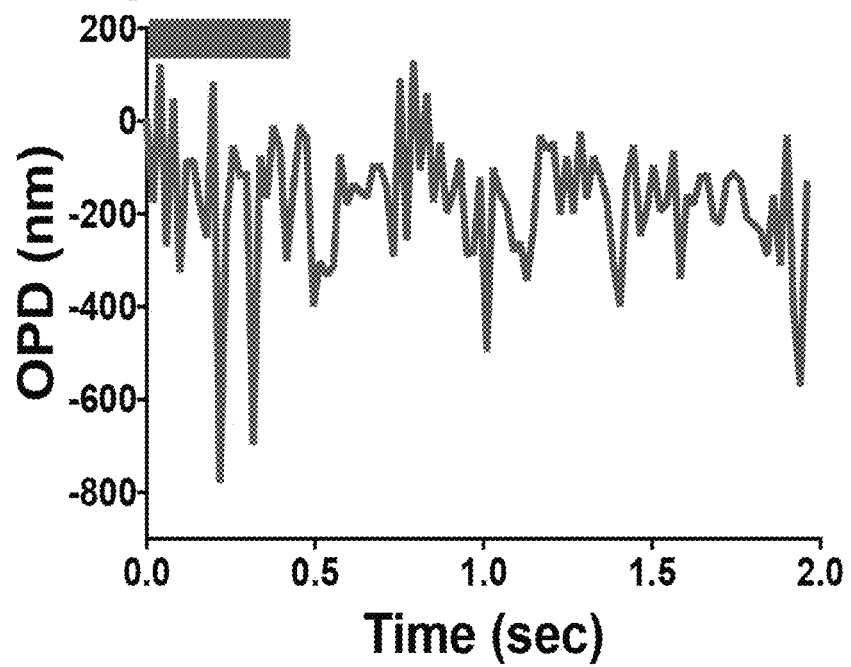
FIG. 3C shows the PSFD-OI response (optical path length difference, OPD) measured with the visual stimulation light on and the stimulation light off.

The camera output is the FD-OI signal S(k) in k-space and is called an A-scan. To obtain the FD-OCT image, I(z) Fourier transform (FT) of the signal S(k) is performed. Multiple A scans were acquired at desired location of retina and OPD was calculated from the optical signal encoded in the phase data. The visual stimulation exposure duration was controlled electronically, which was synchronized with the FDOCT and fundus imaging system. The measured visually stimulated label-free ORG response (optical path length difference, OPD) from retina of a wild type mouse in-vivo. FIG. 3A represents cross-sectional view of the retina and FIG. 3B represents the axially scanned image (A-scan). The different retinal layers are visible. FIG. 3C depicts PSFD-OCT response measured with the visual stimulation light on and the stimulation light off.

Figure 4A:
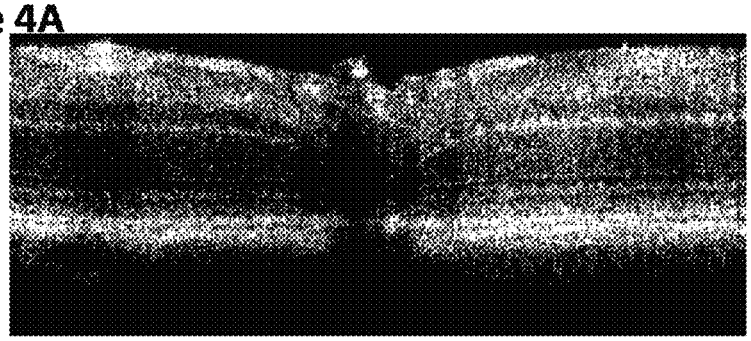
FIG. 4A shows the cross-sectional view of the retina of a ChR2 transgenic mouse in-vivo. The different retinal layers are visible.
Figure 4B:
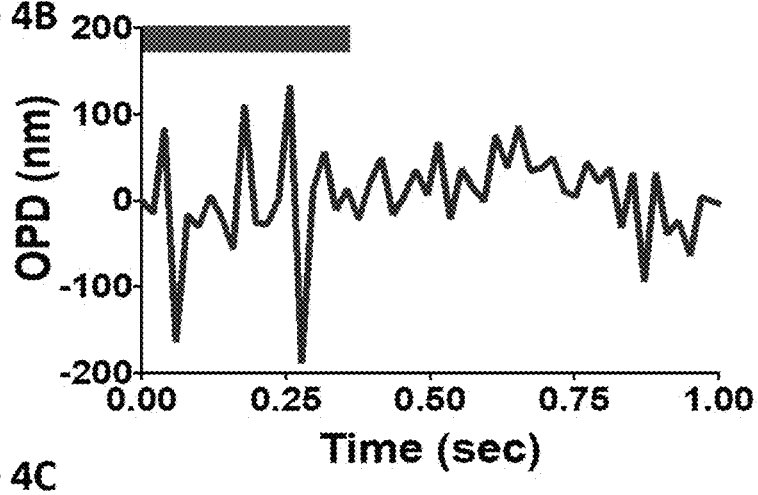
FIG. 4B shows the PSFD-OCT response of retinal layers measured with the visual stimulation light on (red bar) and the stimulation light off.
Figure 4C:
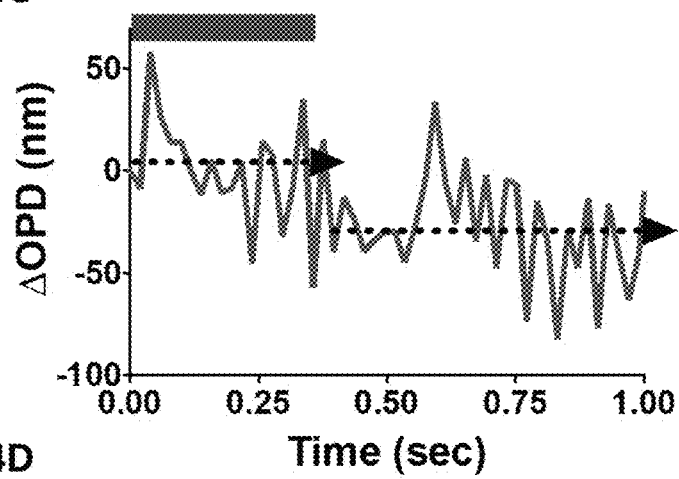
In FIG. 4C, the relative changes of OPD between photoreceptors layer and ganglion cell layer is presented.
Figure 4D:
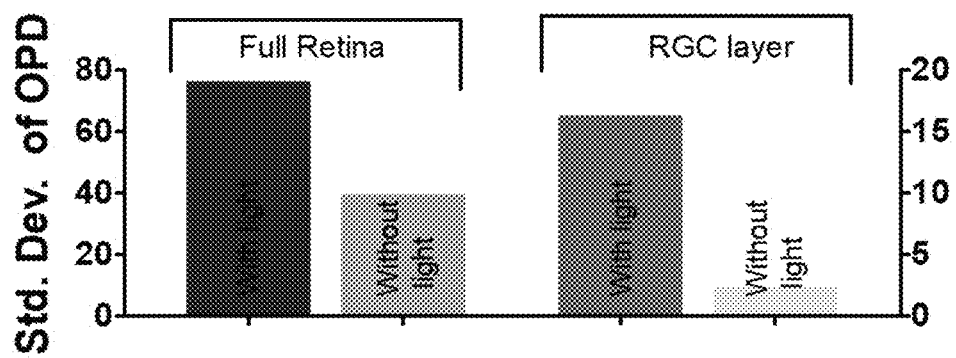
FIG. 4D shows the standard deviation of the OPD signal for full retinal depth scan and RGC specific layer.

In another example, we demonstrate the use of ORG system in case of layer specific activity detection for opsin sensitized mice. The visually stimulated ORG response from different retinal layers of a Channelrhodopsin (ChR2) mouse in-vivo was measured. In FIG. 4A cross-sectional view of the retina is shown. In FIG. 4B, the measured ORG response from specific retinal layer (RGC layer sensitized with Chr2) is shown. In FIG. 4C, the relative changes of temporal optical path length difference (OPD) in presence and absence of visual stimulation between photoreceptors layer and ganglion cell layer is presented. FIG. 4D presents the standard deviation of the OPD signal for full retinal depth scan (average of axial scan from full retinal) and RGC specific layer (average of axial scan from RGC layer).

Figure 5A:
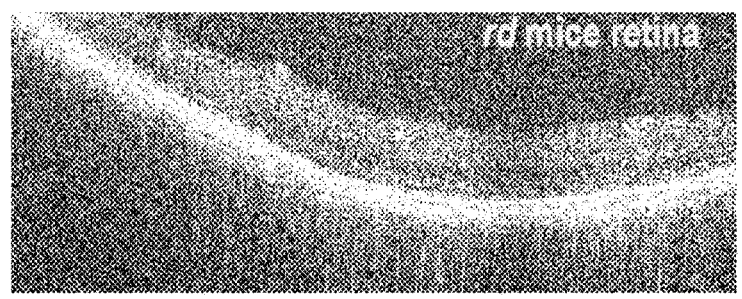
FIG. 5A shows the OCT scanned image of retina of retinal degenerated (rd) mice.
Figure 5B:
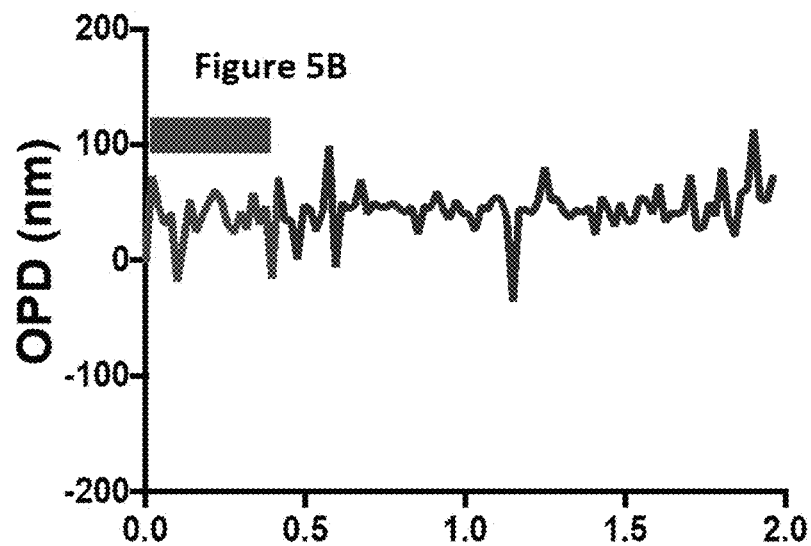
FIG. 5B shows the optical response from the retina in presence (red bar) and absence of visual stimulation.
Figure 5C:
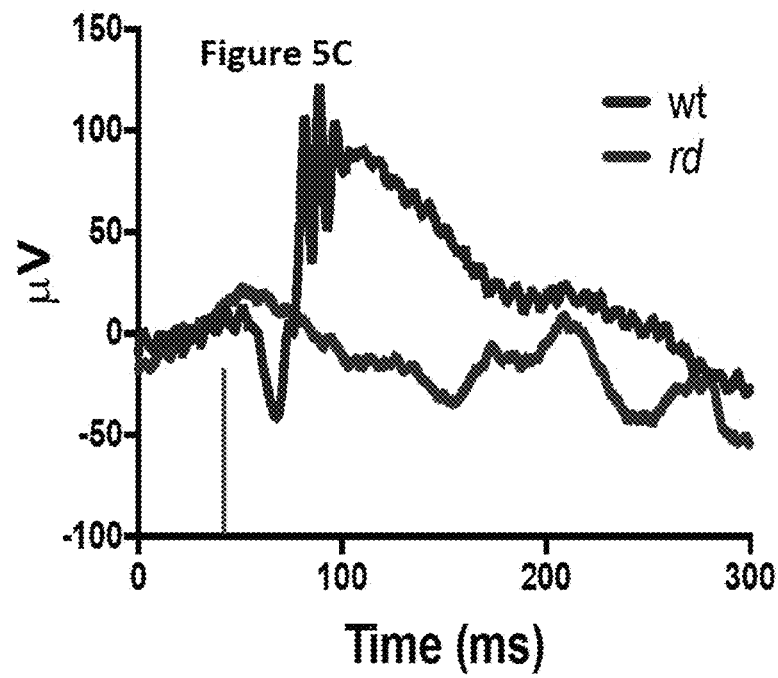
FIG. 5C shows the electroretinogram (ERG) recording on wild type and retinal degenerated mice with light intensity of 6.5 log cd sec/m$^2$. The red vertical line represents the light stimulation point.

In another example, to verify the ORG system reliability, retinal degenerated mice without any photoreceptor were subjected to ORG measurement. In FIG. 5, we show the measured ORG response in rd mouse with retinal degeneration. In FIG. 5 FFORG response collected from rd mice. Cross-sectional view of the rd10 retina in FIG. 5A. In FIG. 5B, axially-averaged ORG response measured with the visual stimulation light on (red) and off (black) is shown. ERG recording on wild type and retinal degenerated mice with light intensity of 6.5 log cd sec/m$^2$ is shown in FIG. 5C. The electrical (FIG. 5C) and optical measurement (FIG. 4B & FIG. 5B) are found to be in good agreement. The visual evoked activity in retina was not detected in the fORG response from the photoreceptor degenerated mice as expected and validates functional measurement capability of the ORG system to assess the functional state of the retina.

The signal to noise ratio for fORG signal relies on numerous factors like reflectively of the probe light, movement of the eye, wavelength and bandwidth of the probing beam. Eye tracking algorithm and faster A scan will minimize the noise and enhance the signal to noise ratio. To enhance visual stimulation efficacy, modulated stimulation of light (square, ramp, triangular) can be used.

Figure 6:
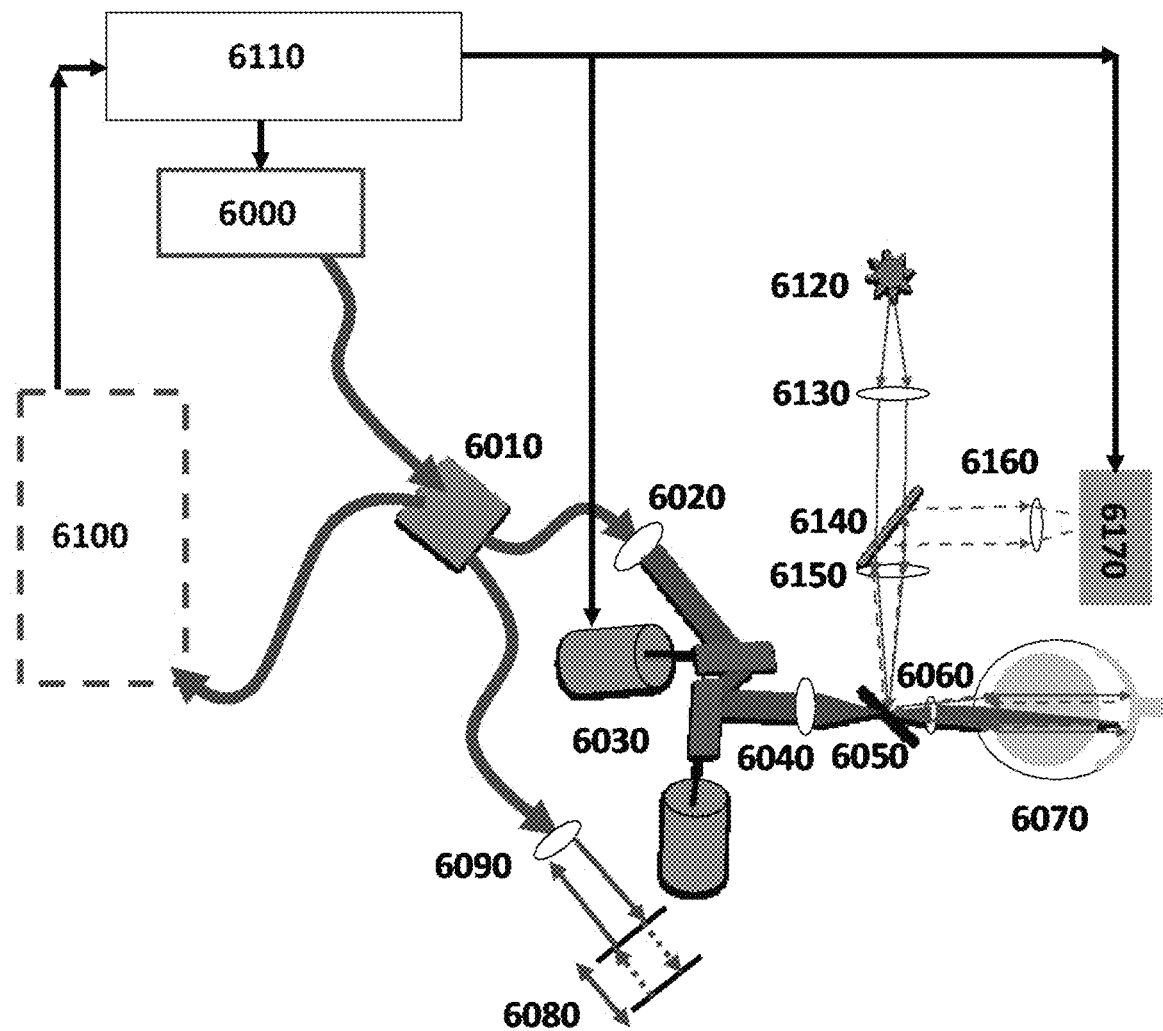
FIG. 6. PS-TD OCT integrated with funduscopic imaging for activity monitoring of retina. 6000: low coherence source (SLD); 6010: Fiber coupler; 6020: collimating lens; 6030: X-Y scanning mirror; 6040: Lens 6050: Dichroic mirror, 6060: Lens 6070: Subject eye; 6080: Reference axial scanning mirror; 6090: Collimating lens; 6100: Photodiode; 6110: Computer, Controller and Display; 6120: Light source; 6130: Condensing lens; 6140: Beam Splitter; 6150: Lens; 6160: Lens; 6170: Camera FIG. 7. PS-TDOCT (for layer-specific functional measurement) integrated with FDOCT (for structural measurement). 7000: low coherence source (SLD); 7010: Fiber coupler; 7020: collimating lens; 7030: X-Y scanning mirror; 7040: Lens 7050: Dichroic mirror, 7060: Lens 7070: Subject eye; 7080: Reference arm mirror; 7090: Collimating lens; 7100: Fiber Spillers 7110: Spectrometer; 7120: Photodiode 7130: Computer, Controller and Display; 7140: Light source; 7150: Condensing lens; 7160: Beam Splitter; 7170: Lens; 7180: Lens; 7190: Camera FIG. 8. Schematic of integrated device for focal/patterned stimulation and PS-FDOCT for activity monitoring. 8000: low coherence source (SLD); 8010: Fiber coupler; 8020: collimating lens; 8030: X-Y scanning mirror; 8040: Lens 8050: Dichroic mirror; 8060: Lens 8070: Subject eye; 8080: Reference arm mirror; 8090: Collimating lens; 8100: Spectrometer; 8110: Computer, Controller and Display; 8120: Light source; 8130: Condensing lens; 8140: Beam Splitter; 8150: Lens; 8160: Lens; 8170: Camera; 8180: Light source for point stimulation; 8190.

In FIG. 6, schematic of time domain ORG system is presented, which will allow locked in detection from a specific retinal layer allowing better spatio-temporal control. The interferometer splits the light from the broadband light source into two paths, the reference and sample arms. The reference arm is terminated by a mirror, which scans in the axial direction. In the sample arm, the light is weakly focused into a sample (retinal layer). The interference signal between the reflected reference light and the backscattered sample light is then recorded. As the light is emitted from a broadband source a strong interference signal is only detected when the light from the reference and sample arms has travelled the same optical distance. Specifically, coherent interference is observed only when the optical path lengths differ by less than the coherence length of the light source, a quantity that is inversely proportional to its optical bandwidth. By axially scanning the reference arm reflector optical sectioning of the sample is performed, allowing for the generation of map of optical reflectivity versus depth. XY scanning using Galvo or MEMS scanner (transverse scanning) of the sample generated 2D and 3D depth profile of the sample.

Figure 7:
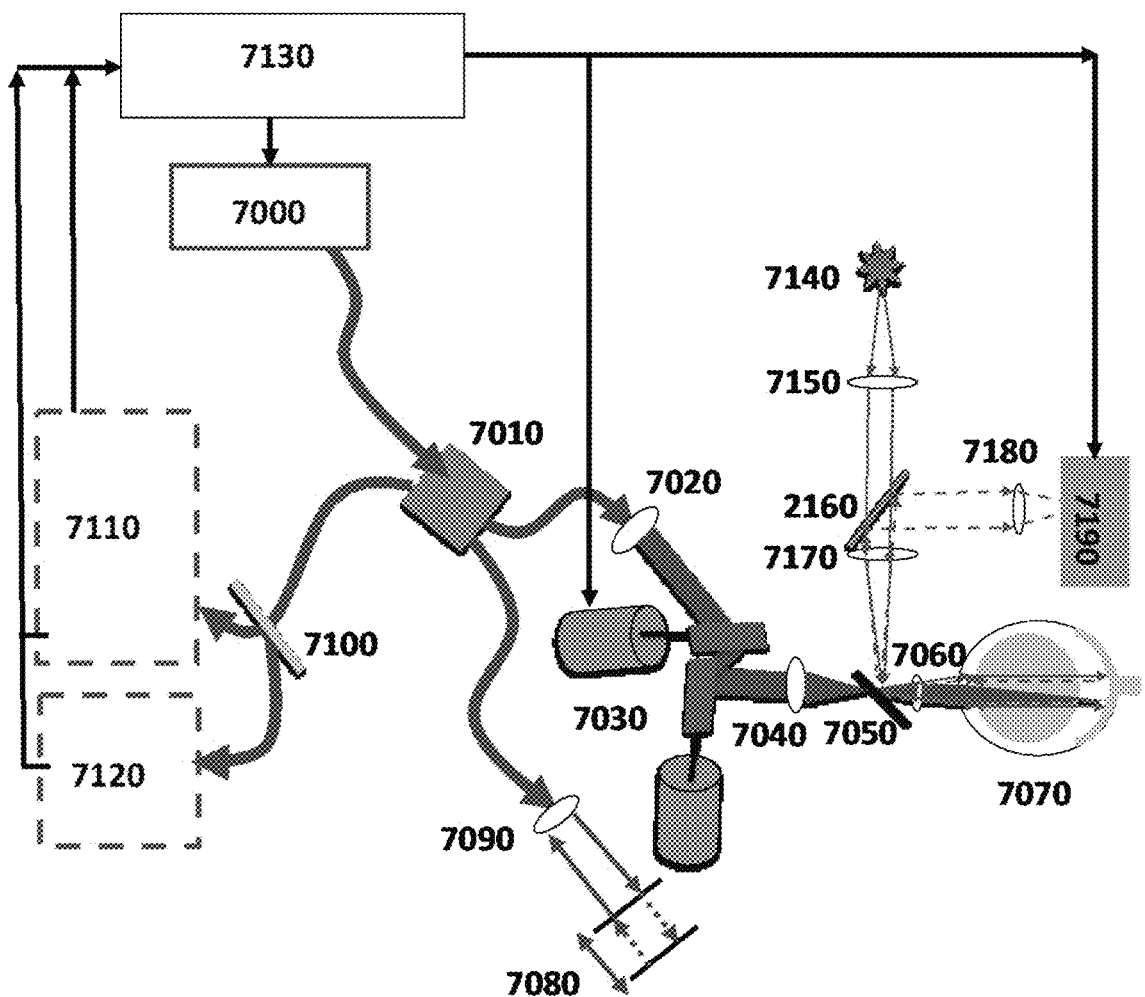

FIG. 7 represents a schematic design for a combined time domain and frequency domain ORG system, which will eliminate motion artifacts (arising due to blood flow and breathing) by using locked-in detection with fixed frequency stimulation, averaging and thresholding of ffORG signal. In the combined setup, the output signal from the broadband light source splits the light from the broadband light source into two paths, the reference and sample arms. The reference arm is terminated by a mirror, which has the optional scanning functionality. In the sample arm, the light is focused into a sample (retinal layer). The interference signal between the reflected reference light and the backscattered sample light is recorded. In the inference light from the reference and the sample arm is split half; one path goes to the photodetector and other part goes to the spectrometer. This configuration allows optional use of time and/or spectral domain interferometry scanning depending on the requirements and obtains function information from the retinal layers.

Figure 8:
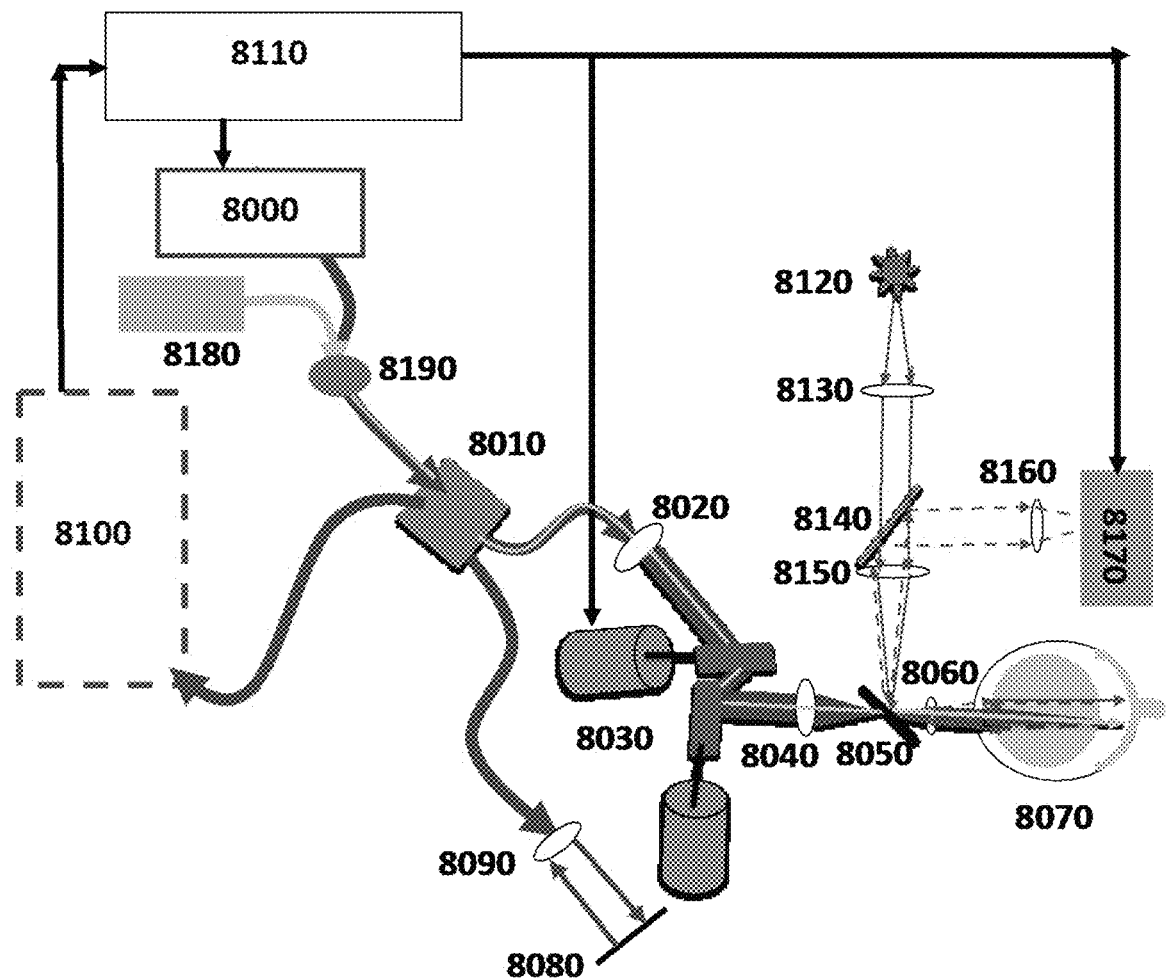
Figure 9:
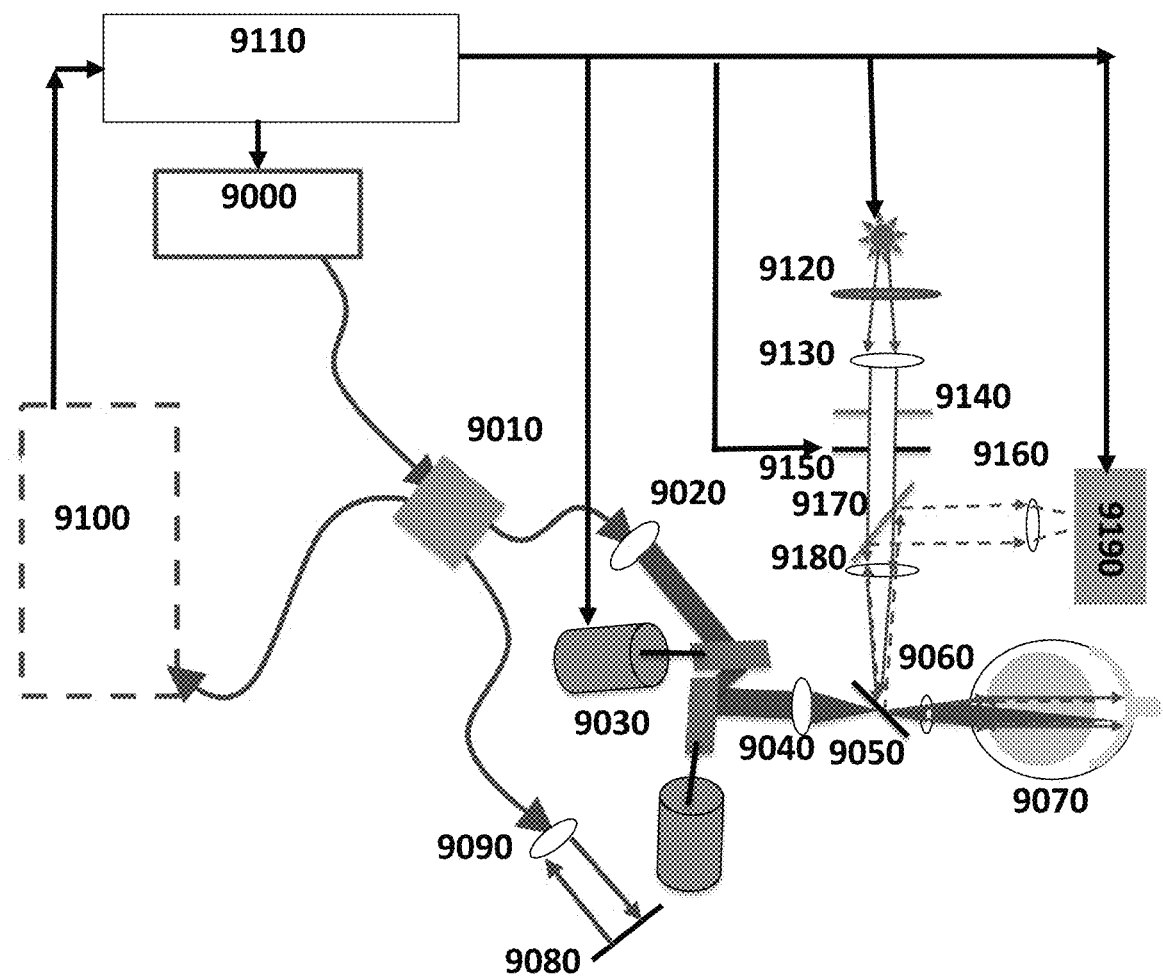
FIG. 9. Schematic of integrated device for visual stimulation and imaging by optical interferometry. 9000: low coherence source (SLD); 9010: Fiber coupler; 9020: collimating lens; 9030: X-Y scanning mirror; 9040: Lens 9050: Dichroic mirror, 9060: Lens 9070: Subject eye; 9080: Reference arm mirror; 9090: Collimating lens; 9100: Spectrometer; 9110: Computer, Controller and Display; 9120: Light source; 9130: Condensing lens; 9140: Aperture control; 9150: Shutter control; 9160: Lens; 9170: Beam Splitter; 9180: Lens; 9190: Camera.

Focal stimulation and focal detection can be achieved by coupling the stimulating beam with the optical probing beam path. FIG. 8 shows use of focal stimulation of retina in conjunction with ORG signal recording. The light source (LED/Laser) is coupled to the input fiber path for coming from the SLD. The configuration allows focal point stimulation of retinal surface while structural-OCT scanning and study the effect of focal stimulation by measuring the retinal activity obtained from the same position as of stimulation As a label-free, non-invasive, non-contact method of the disclosure, a variety of medical applications may be employed including the disease monitoring and diagnosis of various retinal dystrophies. Although, structural diagnostics using OCT provides high-resolution layered structures of the retina, it lacks functional diagnosis of photo-transduction in the retinal circuitry (rods/cones, bipolar and ganglion cells). The current functional diagnostics of retina rely on psycho-physical (e.g. Amsler grid) and electrical (ERG) measurements, which have limitations in assessing local function of specific retinal layers, and thus may miss early onset of the disease progression. The fORG/ffORG system is able to provide functional data, which will indicate the functional state of retina (healthy/early state retinal disorder). Successful detection of early stage photoreceptor loss provides windows for applying therapeutic treatment to arrest or slowdown retinal degeneration.

In some cases, the targeted mammalian subject's retina can be visually stimulated at a desired focal point or global area and A-scan data can be collected to observe the effect of focal/global light stimulation. Focal or Global stimulation may comprise of UV light, invisible light, visible light or infrared (IR) or near-infrared (NIR) light. Stimulation can be under photopic, scotopic or mesopic condition. Alternatively, the retinal activity can be triggered or stimulated using ultrasonic wave and use of magnetic field in retina sensitized with tailored magnetic particles.

In yet another embodiment of the present disclosure, fORG/ffORG scan is performed on multiple points in a selected area in the target. In some examples, one or more beams of stimulated light are used can be patterned on to the retina using spatial light modulator (SLM). The fORG/ffORG scan can be carried out on retina to measure activity from temporal variation of optical signal. Stimulation light source can have controllable light power, which is controlled by optical neutral density filter or variable current input for the light source. The stimulation light wavelength can be controlled electronically (by a using combination of color LED) or using a band pass filter into the light path or tunable super continuum light source.

In retinal degenerative diseases such as dry age-related macular degeneration (dry-AMD) and Retinitis Pigmentosa (RP), the photoreceptors (e.g., rods and cones) that are responsible for conversion of light into electro-chemical signals, are degenerated. This prevents the generation of photo-induced signals in retina. Loss of photoreceptor cells and/or loss of photoreceptor cell function are the primary causes of reduced light sensitivity and blindness. Clinical translation of current optogenetics approach for treatment of blindness using opsin-encoding genes into degenerated-retina (macula in dry-AMD (39-43)) has shown promise in animal models. fORG/ffORG provides label-free, non-invasive, non-contact methods to evaluate the efficacy of such gene therapy treatment for various retinal disorders such as but not limited to dry-AMD, RP.

In yet another embodiment of the disclosure, determining the diseases state (such as retinal dysfunction) is performed by comparing or using a reference such as data from healthy functional retina. fORG and ffORG scan can be performed on the normal healthy retinal area(s) to generate reference data sets for healthy retinal activity. The above-described procedure can be repeated in blind subjects. For example, in case patients who underwent opsin-based gene therapy, the retinal function of the treated subjects can be monitored over time to measure of the efficacy of treatment by comparing activity with the normal healthy subjects. In another aspect, the same procedure can be applied to monitor disease progression (slow versus fast degeneration). In other aspect of the disclosure, complete spectral analysis is performed to extract a full set of optical properties of the target such as phase, amplitude, frequency of the detected optical signal form the retina. Medical decision can be made based on the functional (fORG, ffORG) and or structural (OCT) data.

In yet another embodiment of the disclosure, the described fORG/ffORG system is a configured device which may consists of the following: mounted or hand help probe, funduscopic imaging, laser or light source coupled to optical scanning, light source (SLD, or swept source), stimulation light with or without spatial light modulator (SLM). Other aspect of the disclosure provides determination of physio-chemical change occurring in various retinal layers under light stimulation under photopic or scotopic condition. Comparative analysis on different retinal layers (ONL: Outer Nuclear Layer, INL: Inner Plexiform Layer, GCL: Ganglion Cell Layer) and their relative position calculated by phase measurement will provide valuable information such as swelling of layer (s) under healthy or diseased retina.

The terms "focused functional ORG" and "fORG," described herein, generally refer to a method of optical interference scanning comprising both structural (tomographic and cross-sectional information) and functional information of retinal layers. The disclosed method may utilize any method of optical coherence tomography. Generally, fORG is configured with an interferometer and spectrometer or photodiode, as is the case in many other optical interferences-based methods. Low coherence broadband light from a light source is split (by fiber coupler or beam-splitter), one split beam goes along a sample arm (subject to be interrogated e.g. eye) and other as a reference arm (comprising a mirror). FIG. 2 depicts various part of the integrated fORG system. Spectral domain implementation of the low coherence optical interferometry is capable collecting and processing phase information contained in the intrinsic back-reflected optical signals. In the PSFD-OI, reference mirror is stationary and the interference signal between the reflected intensities from the reference mirror and the sample microstructures is detected with a spectrometer as a function of wavelength. The detected signal (as a function of wavelength) is then Fourier transformed to obtain intensity profile as a function of depth. PSFD-OI scans the whole depth of the sample without any mechanical scanning, which leads to higher phase stability. The schematic diagram of our phase sensitive FD-OI system is shown in FIG. 2. It uses a broadband super luminescent diode (SLD, central wavelength: 860 nm and bandwidth: 150 nm, which leads to an axial resolution of ~2 µm in air). The high axial resolution enables in-vivo detection of visual stimulation induced nano-changes of specific retinal layers.

The light from the SLD is connected 2×2 coupler as shown in the FIG. 2. One of the outputs of the coupler goes to a reference arm and the other goes to the sample arm. Sample beam power of ~800 µW was used. The sample arm consists of a XY galvo/MEMS scanner and objective lens (the objective lens NA is 0.12, focal length: 4 mm; working distance: 3 mm.) The reference arm consists of a collimator, which collimates the light from the fiber and a lens that focuses the light on to a mirror. The reflected light from the reference arm and the sample arm go back to the 2×2 coupler and to the connected to the spectrometer. The spectrometer consists of another collimator that collimates the light emanating from the fiber, followed by a transmission grating to spectrally spread the signal. A lens is used to focus the dispersed signal to a line-scanning camera (1024 pixels). The camera output is the FD-OCT signal S(k) in k-space and is called an A-scan. In order to obtain the FD-OCT image, I(z) Fourier transform (FT) of the signal S(k) is performed.

The devices, methods, and systems of the disclosure provide a mean for quantitatively monitoring functional retinal activity. fORG/fORG Signal Processing and Analytical Method is described below to extract intrinsic optical information from A-scans.

Spectral interference signal generated from the retinal layer(s) can be written as, $$S_o(k,t) = \alpha S_i(k)\{R_1 + R_2 + 2\sqrt{R_1 R_2}|\mu(k)|\cos[\phi(k,t)]\} \quad (Eq.\ 1)$$

where, $S_i$ is the spectral density of the broadband light source, $\alpha$ is the coupling efficiency of reflected light from the retinal layer to the interferometer, and k $(=1/\lambda)$ is the wavenumber. $R_1$ and $R_2$ are the reflectivity of the bottom and top interfaces of the cell culture device, respectively. $\mu(k)$ is the spectral coherence function and $\phi(k,t)$ angular phase difference proportional to the optical path difference (OPD) between top and bottom interfaces of the cell culture device given by the expression, $$\phi(z,t)|_{z=d} = \frac{4\pi}{\lambda_c} p(z,t) = \tan^{-1}\left\{\frac{\mathrm{Im} S_0(z,t)}{\mathrm{Re} S_0(z,t)}\right\} \quad (Eq.\ 2)$$

where, p(z,t) is the OPD and $S_o(z)$ is the Fourier transform of Eq.1 calculated at the peak value of the coherence function corresponding to spatial location of the retinal layer z=d.

A data acquisition card and software interface is used for data collection. Spectral interferograms (A scans at a fixed point) are digitized and stored raw files for post-processing. Each spectral interferogram is Fourier transformed and phase at a spatial frequency channel corresponding to a particular retinal layer is calculated as a function of time, $\phi(d,t)$. Temporal phase difference $(\Delta\phi(d,t_n))$ at a given time was calculated by subtracting the measured phase of A-Scan at time $t_n$ from the first (baseline) A-Scan at the start of the experiment. Change in OPD is calculated from the phase difference by, $$\Delta p(d, t_n) = \frac{\lambda_c}{4\pi} \Delta\phi(d, t_n) = \frac{\lambda_c}{4\pi}[\phi(d, t_n) - \phi(d, t_0)] \quad (Eq.\ 3)$$

FIG. 2 shows a schematic diagram of the basic fiber-based fORG setup. The interferometer splits the light from the broadband light source into two paths, the reference and sample arms. The reference arm is terminated by a mirror, which scans in the axial direction; in the sample arm, the light is weakly focused into a sample (retinal layer). The interference signal between the reflected reference light and the backscattered sample light is then recorded. As the light is emitted from a broadband source a strong interference signal is only detected when the light from the reference and sample arms has travelled the same optical distance. Specifically, coherent interference is observed only when the optical path lengths differ by less than the coherence length of the light source, a quantity that is inversely proportional to its optical bandwidth. By axially scanning the reference arm reflector optical sectioning of the sample is performed, allowing for the generation of map of optical reflectivity versus depth. XY scanning using Galvo or MEMS scanner (Transverse scanning) of the sample generated 2D and 3D depth profile of the sample.

The spatial variation of refractive index in tissues exhibits multifractality (20) and disease progression is exhibited by distinct changes in multifractal parameters (generalized dimension and width of the singularity spectrum, WSS). We have developed FFORG device for acquiring intensity/phase-OCT data during focal visual stimulation of retina. Our innovation is based on in-depth multifractal analysis of these spatial-varying data as follows. Multifractality of nanostructural changes in 2D-spatial distribution of reflected light intensity (measured by B-scan) was measured as follows: Locally-connected fractal dimension ($D_{LC}$) analysis uses pixel mass from concentrically placed sampling units, using the connected set at each pixel to produce a distribution of local variation in complexity. FIG. 10F shows the map of $D_{LC}$ of B-scan OCT intensity retina image, calculated for each pixel using the slope of the log-log regression line for pixel mass against box size. The multifractality variations (represented by the color map) in different retinal layers (high in photoreceptor and pigment layer as compared to ganglion and inner nuclear layers) and within the same layer demonstrated the nanostructural variations, which changes during disease progression.

Figure 11A:
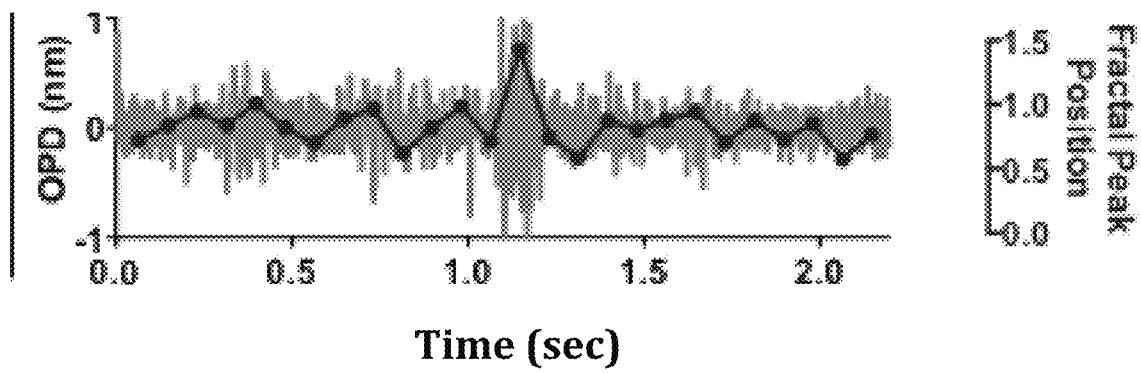
FIG. 11A shows the variation of measured multifractal spectrum (Dh vs h) peak position (blue line) overlaid on temporal change in OPD (gray). The pharmacological modulation of neural activity could be measured by phase OCT and multifractal analysis.
Figure 11B:
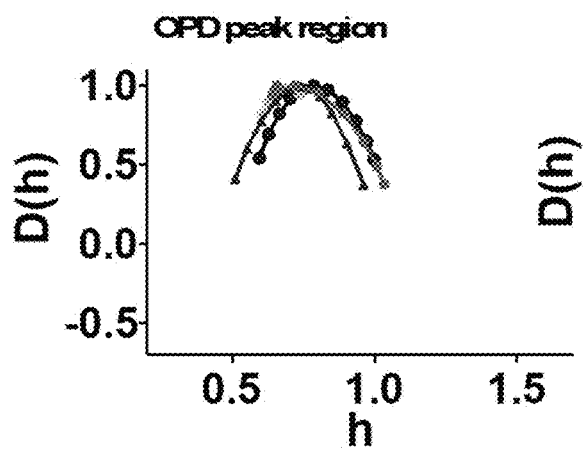
FIG. 11B shows the multifractal spectrum of OPD peak regions and FIG. 11C shows the multifractal spectrum of the non-peak regions.
Figure 11C:
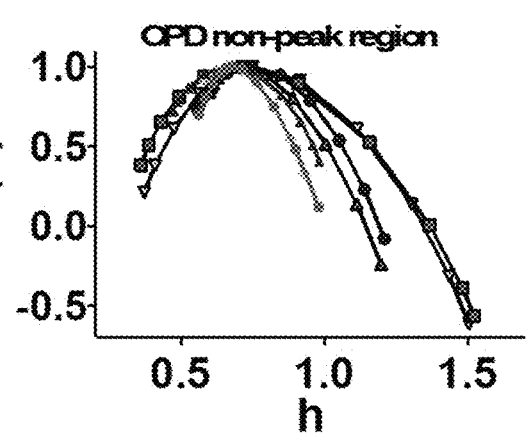
Figure 11D:
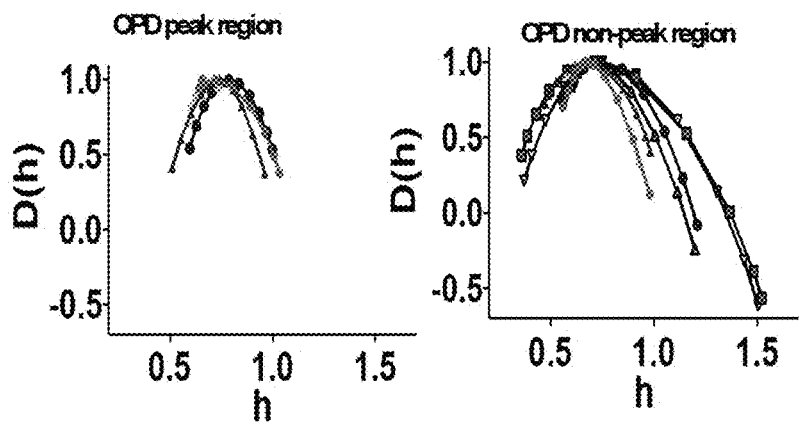
FIG. 11D shows the quantitative comparison of width of the multifractal spectrum between OPD peak and non-peak regions. *p<0.05.

Further, our innovation is based on in-depth multifractal analysis of temporal-varying intensity/phase-OCT data as follows. Multifractality in time-varying reflected light intensity from different layers (measured by A-scans) was measured as follows: In multifractal analysis of A-scan OCT images, we utilize Generalized dimension ($D_q$) to address how intensity varies with $\varepsilon$ (resolution). In particular, it is a distortion of the mean ($\mu$) of the probability distribution for pixels at some $\varepsilon$. To calculate it, $\mu$ is exaggerated by being raised to some arbitrary exponent (q), then compared again to how this exaggeration varies with $\varepsilon$. These measures help characterize the variety within a pattern in as much as it depends on the scale at which the pattern is observed. In FIG. 10C we show multifractal spectrum (plot of $D_q$ versus q) at an arbitrarily targeted spot on wild type mouse retina. In case of mono-fractal behavior, the plot of $D_q$ versus q tends to be horizontal rather than sigmoidal and decreasing (as in multifractal, FIG. 10C). We discovered that $D_{q=2}$ changes significantly upon focal light stimulation (FIG. 10D). The pharmacological modulation of neural activity could be measured by phase OCT and multifractal analysis. FIG. 11A shows the variation of measured multifractal spectrum (Dh vs h) peak position (blue line) overlaid on temporal change in OPD (gray). FIG. 11B shows the multifractal spectrum of OPD peak regions and FIG. 11C shows the multifractal spectrum of the non-peak regions. FIG. 11D shows the quantitative comparison of width of the multifractal spectrum between OPD peak and non-peak regions. *p<0.05.

Multifractality in temporal fluctuations in optical path difference (measured by PS-OCT): Though nanoscale optical path difference can be measured using PS-OCT, we discovered that the multifractal spectrum ($D_h$ vs h) provides a distinct measure of how much the local regularity of the PS-OCT signal varies in time. The multifractal signal from PSOCT signal (OPD in photoreceptor layer) exhibits variations in signal regularity over time and has a multifractal spectrum with wider width (FIG. 13D, baseline). However, a less multifractal signal exhibits essentially the same regularity everywhere in time and therefore has a multifractal spectrum with narrow width (FIG. 13D, light stimulation).

FIG. 13E shows statistically significant differences in width of singularity spectrum (WSS) in absence and presence of focal light stimulation In some examples, fORG will use swept-source instead of super luminescence diode. Swept source interferometry uses a short-cavity swept laser having center wavelength at approximately ~1 μm and it changes continuously when it sweeps across a narrow band of wavelengths with each scan. Instead of a spectrometer, a complementary metal oxide semiconductor camera is used, along with two fast parallel photodiode detectors, which allows higher scan speed enabling superior temporal resolution in data collection. A major advantage of the system will allow retinal activity measurement in a stable condition with minimal the motion artifact.

In some examples, different patterns of light spots will be projected on to the retinal explant using Digital micro-mirror device (DMD) or spatial light modulator (SLM). Light induced ORG response at different light intensities and frequencies can be used. The signals from retina in presence and absence of light stimulation pattern will be characterized to assess the retinal functional state and disease state.

FIG. 3C shows the measured visually stimulated response (optical path length change, ΔOPL) from retina in-vivo. The visual stimulation exposure duration was controlled electronically, which was synchronized with the fundus imaging system. The measured visually stimulated label-free ORG response (optical path length difference, OPD) from retina of a wild type mouse in-vivo. (A) Cross-sectional view of the retina (i) and the point scan (A-scan) image (ii) for optical detection. The different retinal layers are visible. (C) fORG response measured with the visual stimulation light on and the stimulation light off.

According to the methods described herein, fORG/ffORG may be used to provide a medical decision for Retinal degenerative diseases. In one embodiment, the present disclosure provides methods of detecting disease state like retinal degeneration where photoreceptors and visual sensitivity is lost. fORG can be applied in medical disease assessment related to a variety of retinal dystrophies that may include but is not limited Age-related macular degeneration (AMD), Retinitis Pigmentosa (RP), Leber Congeneital Amaurosis (LCA), rod-cone dystrophy, Stargardts's disease, laser-injured scotoma, photodegenerated retina, blast-injured retina, Ocular trauma injury, retinoblastoma, diabetic retinopathy, Glaucoma-related injury.

Currently, use of optogenetic sensitization of retinal cells combined with activation/inhibition has allowed the possibility of replacing the retinal implants, eliminating the requirement of placing electrodes near every single neuron for high resolution (44). Optogenetic stimulation provides high temporal precision (22, 45-49) by introducing light-activatable molecular channels (opsins) into cells by genetic targeting. In addition to higher temporal and spatial resolution, optogenetics has several advantages over electrical stimulation such as cellular specificity (e.g. spared cones, ganglion or bipolar cells) and minimal invasiveness (50). This optogenetic activation method is very promising for controlling cellular activities in-vitro as well as in-vivo as it only requires light of moderate intensity that can be delivered from a light emitting diode (LED) or laser (45, 46). Various light-activated ion channels (opsins) have been developed to either enhance photosensitivity of cells, or to be activated by different wavelengths of visible light.

Vision restoration by optogenetics or other gene therapy methods has been proposed in humans by delivery of opsin or other genes via viral means (e.g. recombinant adeno-associated virus, or lentivirus) in to the vitreous or sub-retinal space of the eye. Since opsin gene delivery does not alter the retinal structure, the present invention of a layer-specific functional evaluation of opsin-sensitized bipolar cells and downstream RGC cells is crucial to assess the success of opsin-delivery, recovery of visual function and monitoring of opsin-retention and any changes to retinal circuitry. Therefore, there is a need for deployment of new and efficient non-viral method that can deliver large constructs to spatially targeted regions of retina in a minimally invasive manner.

ADDITIONAL EXAMPLES

Example 1

An example of retinal diagnosis would include photoreceptor degenerated disease. A fORG/ffORG system can be utilized for functional recovery of diseases such as RP. For examples where opsin is used for treatment of disease is blindness caused by retinal photo-degenerative diseases. Retinitis Pigmentosa (RP) and dry age-related macular degeneration (dry-AMD) refer to disorders characterized by degeneration of photoreceptors in the eye that hinders visual ability by non-functional neuronal activation and transmission of signals to the visual cortex (4, 5, 51-53). While (dry) AMD is the leading cause of new vision loss in ~15 million persons older than 65 years of age (1), the prevalence of RP is at least one million individuals world-wide (54, 55). RP is most often inherited as an autosomal recessive trait with large number of cases having this form of inheritance (52, 54, 56). Further, the degree of visual loss increases with ageing (57) and this is a major concern for demographic changes towards elderly population. Furthermore, The most effective way to tackle glaucoma is via early stage detection since there is no neuroprotective agent approved for commercial use. Glaucoma is a leading eye disorder which has few symptoms and difficult to detect in early stages. Unfortunately it leads to damage of the optic nerve leading to initial peripheral vision loss or ultimately to irreversible vision loss causing permanent blindness. Currently, more than 3 million Americans are suffering from glaucoma. Globally, ~70 million individuals have glaucoma and this number is expected to reach near 80 million by 2020.

Example 2

FIG. 2 shows Schematic of set up for ffORG is based on spectral domain implementation of the optical interferometry system that was recently developed in the OCT research community (38, 58-61), and analyzes the phase information contained in the back reflected optical signals. Using interferometry based technique, it is shown to be possible to measure sub-nanometer motion of the cells (38). In the phase sensitive interferometry, reference mirror is stationary and the interference signal between the reflected intensities from the reference mirror and the sample microstructures is detected with a spectrometer as a function of wavelength. The detected signal (as a function of wavelength) is then Fourier transformed to obtain intensity profile as a function of depth. FD-OCT scans the whole depth of the sample without any mechanical scanning, which leads to higher phase stability. The schematic diagram of our various modality of fORG/ffORG systems are shown in FIG. 2, FIG. 6, FIG. 8, and FIG. 9. The high axial resolution enables in-vivo detection of visual stimulation induced nano-changes of specific retinal layers.

The light from the SLD is connected to port 1 of a circulator and port 2 of the circulator is coupled into an arm of fiber coupler as shown in the FIG. 1. One of the outputs of the coupler goes to a reference arm and the other goes to the sample arm. Sample beam power of ~800 µA was used. The sample arm consists of a XY galvo-scanner and objective lens. The reference arm consists of a collimator, which collimates the light from the fiber and a lens that focuses the light on to a mirror. The reflected light from the reference arm and the sample arm go back to the 2×2 coupler and into the port 2 of the circulator. Port 3 of the circulator is connected to the spectrometer. The spectrometer consists of another collimator that collimates the light emanating from the fiber, followed by a transmission grating to spectrally spread the signal. A lens is used to focus the dispersed signal to a line-scanning camera. The camera output is the optical signal in k-space and is called an A-scan, which is further analyzed to obtain functional information.

Example 3

FIG. 3A shows the Cross-sectional view of the retina of a wild type mouse in-vivo and FIG. 3B shows the point scan (A-scan) image for optical detection. The different retinal layers are visible. FIG. 3C shows the measured visually stimulated response (optical path length change, OPD) from retina in-vivo. The visual stimulation exposure duration was controlled electronically, which was synchronized with the FDOCT and fundus imaging. The measured visually stimulated label-free ORG response (optical path length difference, OPD) from retina of a wild type mouse in-vivo.

Next, we show an example of use of fORG/ffORG system capable of measurement of the nano-fluctuation of the cells in specific layer. Due to low coherence length of the source, the method can isolate the layer of interest with high spatial localization enabling us to track the optically-induced nano-fluctuation of targeted cells in specific layer. The retina cross-sectional image was divided into different layers segment. FIG. 4A shows the cross-sectional view of the retina of a ChR2 transgenic mouse in-vivo. The different retinal layers are visible. FIG. 4B shows the PSFD-OCT response of retinal layers measured with the visual stimulation light on (red bar) and the stimulation light off. FIG. 4B represents the measured OPD signal from the composite of retinal with time. In FIG. 4C, the relative changes of OPD between photoreceptors layer and ganglion cell layer is presented. FIG. 4D shows the standard deviation of the OPD signal for full retinal depth scan and RGC specific layer.

The ORG signal (i.e. change in OPL) is a convoluted change in physical path length and refractive index in retina during visual stimulation. Change in membrane potential (hyperpolarization) of photoreceptor cells and decrease in intracellular sodium and calcium ions occur via photo-transduction, which can alter refractive index of the photoreceptor layer. A decrease in the intracellular calcium concentration in photoreceptors slows the release of glutamate (via calcium-induced exocytosis) to the bipolar cells, which can either depolarize or hyperpolarize depending on the type of bipolar cells. Finally, the innermost retinal ganglion cell layer transmit the action potential via their axons to the visual cortex. Since cellular deformation is known to occur during action potential propagation, physical change in cell thickness in RGC layer is expected. Our optical interferometry-based label-free ORG measurements (~2 fps) are compound spatio-temporal changes in multiple soma/axons.

Example 5

The retina image of rd10 mice with complete photo-degeneration is shown in FIG. 5A. The rd10 mice (retinal degeneration 10, spontaneous missense point mutation in Pde6b) have a later onset and progressive retinal degeneration, closer to the human retinal photo-degeneration phenotype. FIG. 5B shows the optical response from the retina in presence (red bar) and absence of visual stimulation. The magnitude of ORG response in rd10 mice is significantly lower than that in wild type as shown in FIG. 3C. FIG. 5C shows the electroretinogram (ERG) recording on wild type and retinal degenerated mice with light intensity of 6.5 log cd sec/m$^2$. The red vertical line represents the light stimulation point.

Example 6

The following example illustrates that the multifractality calculated from the time varying A scan changes profoundly upon visual stimulation and thus, can be a useful method for determining visual function. For functional assessment of retina, the transverse location in retina was selected from the B-scan intensity-OCT image and time-series of A-scan images were collected under non-stimulated (FIG. 10A) and stimulated (FIG. 10B) conditions. The raw A-scan image was processed to obtain quantitative phase fluctuations over time, which was analyzed using multifractal algorithm to obtain fractal dimensions (Dq, FIG. 10C). As shown in FIG. 10D, the fractal dimension (Dq at q=−2) is modulated upon visual stimulation validating the analytical method for identifying the functional/active state of the retina. Further, B-scan intensity-OCT image from a retina (FIG. 10E) was processed to yield locally connected multifractal map (FIG. 10F) calculated for each pixel using the slope of the log-log regression line for pixel mass against box size. The locally connected multifractality variations (represented by the color map, FIG. 10F) in different retinal layers and within the same layer can be useful to identify the nerve fiber thinning site.

Example 7

In the following example, we demonstrate that the multifractal ffORG response differs in mouse with retinal degeneration compared to the wild type: FIG. 12A and FIG. 12F shows the structure (FDOCT scanned image) of retina in wild type (wt) and rd10 mice respectively. The whole retina and (photoreceptor) layer-specific phase-FFORG response in presence and absence of visual stimulation for wt and rd10 mice shows that the phase (OPD) fluctuations are higher in wt mice as compared to rd10 mice. Form the OCT scan image, the calculated fractal dimension (Dh vs h) are presented in FIG. 12D and FIG. 12E. The in-depth multifractal analysis (FIG. 12E vs. FIG. 12J) shows that WSS of multifractal spectrum does not change with light stimulation in case of rd10 mice in contrast to the results obtained in wt mice. For functional assessment of RGC layer, the transverse location in retina was selected from the B-scan intensity-OCT image (FIG. 13A) and time-series of A-scan images were collected (FIG. 13B) under stimulated and non-stimulated conditions. From the A-scan interferogram, phase information was extracted and processed to obtain the time-varying OPD signal (FIG. 13C). In case of RGCs, we discovered that in absence of light the OPD fluctuations in ganglion cell layer exhibits less multifractality and therefore, small WSS. In presence of photo-transduction, WSS of ganglion cell activity increased significantly (FIG. 13D) implying increase in multifractality. FIG. 13E shows statistically significant differences in WSS in absence and presence of focal light stimulation.

Example 8

Figure 14A:
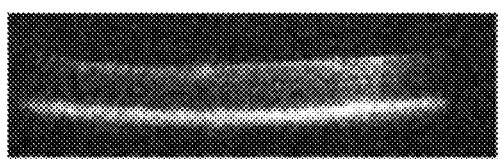
FIG. 14A show the B-scan intensity OCT image of retina.
Figure 14B:
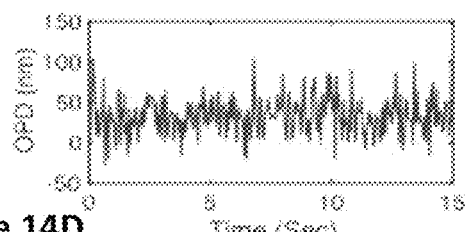
FIG. 14B shows the OPD fluctuation of RGC layer.
Figure 14C:
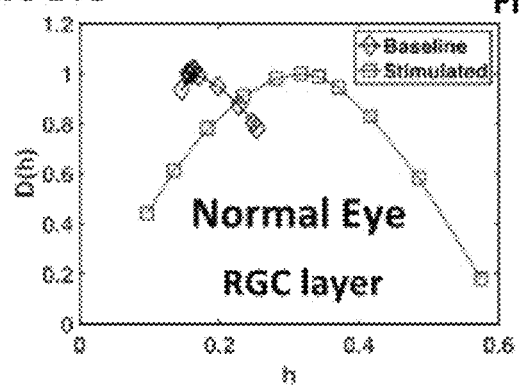
FIG. 14C shows the Variation of measured multifractal singularity spectrum (Dh vs h) of RGC layer activity in absence and presence of light stimulation in Control (un-injured) eye.
Figure 14D:
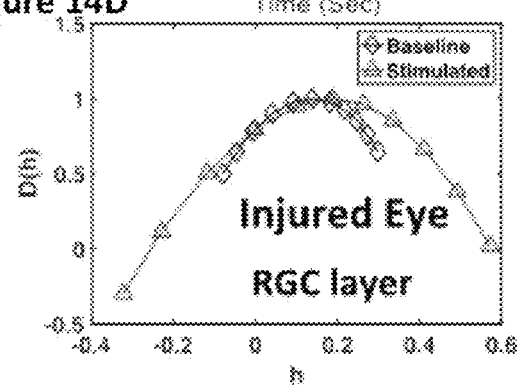
FIG. 14D shows the Variation of measured multifractal singularity spectrum (Dh vs h) of RGC layer activity in absence and presence of light stimulation in ischemia/reperfusion-injured eye.

In another example, the multifractal based disease detection is further validated in ischemia/reperfusion (I/R) injured mice with functional defects in RGC layer was used since the I/R injury model is known to exhibit decreased ERG b-wave amplitudes (62). A number of diseases and conditions are associated with retinal ischemic injury, including retinal vessel occlusion, diabetic retinopathy, and glaucoma. In this case, the reduction of the fractal dimension was part of a medical intervention. The ffORG and multifractal analysis of RGC layer activities in normal vs. I/R injured eyes is included here. The normal eye RGC activities as measured by OPD fluctuations show monofractal behavior, which became multifractal upon photo-transduction as shown in the increased width of the D(h) vs. h multifractal spectrum (FIG. 14C). The change in width of singularity spectrum ($D_h$ vs h) of RGC layer in I/R injured eye was not prominent in presence of light stimulation (FIG. 14D).

For optogenetic vision restoration, patient-to-patient variability and time-dependent changes in spatial-distribution of retinal-degeneration demands site-specific expression of the opsin. Since opsin gene delivery does not alter the retinal structure, a layer-specific functional evaluation of opsin-sensitized bipolar cells and downstream RGC cells is crucial to assess the success of opsin-delivery, recovery of visual function and monitoring of opsin-retention and any changes to retinal circuitry. Therefore, application of ffORG for targeted stimulation and detection in degenerated retina will allow photo-understanding the functional recovery and retinal circuitry rewiring.

The specification and examples herein provide a complete description of the structure and use of illustrative embodiments. Although certain embodiments have been described with a certain degree of particularity, or with reference to one or more individual embodiments, those skilled in the art could make numerous alterations to the disclosed embodiments without departing from the scope of this invention. As such, the various illustrative embodiments of the devices are not intended to be limited to the particular forms disclosed. Rather, they include all modifications and alternatives falling within the scope of the claims, and embodiments other than the one shown may include some or all of the features of the depicted embodiment. For example, components may be omitted or combined as a unitary structure, and/or connections may be substituted. Further, where appropriate, aspects of any of the examples described above may be combined with aspects of any of the other examples described to form further examples having comparable or different properties and addressing the same or different problems. Similarly, it will be understood that the benefits and advantages described above may relate to one embodiment or may relate to several embodiments.

While the compositions and methods of this invention have been described in terms of preferred embodiments, it will be apparent to those of skill in the art that variations may be applied to the compositions and/or methods and in the steps or in the sequence of steps of the method described herein without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the present invention.

Furthermore, the claims are not intended to include, and should not be interpreted to include, means-plus- or step-plus-function limitations, unless such a limitation is explicitly recited in a given claim using the phrase(s) "means for" or "step for," respectively.

The particular embodiments disclosed above are illustrative only, as the application may be modified and practiced in different but equivalent manners apparent to those skilled in the art having the benefit of the teachings herein. It is therefore evident that the particular embodiments disclosed above may be altered or modified, and all such variations are considered within the scope and spirit of the application. Accordingly, the protection sought herein is as set forth in the description. It is apparent that an application with significant advantages has been described and illustrated. Although the present application is shown in a limited number of forms, it is not limited to just these forms, but is amenable to various changes and modifications without departing from the spirit thereof.

REFERENCES

The following references, to the extent that they provide exemplary procedural or other details supplementary to those set forth above, are specifically incorporated by reference.

1. Curcio C A, Medeiros N E, Millican C L. Photoreceptor loss in age-related macular degeneration. Invest Ophthalmol Vis Sci. 1996; 37(7):1236-49.
2. Barteselli G, Gomez M L, Doede A L, Chhablani J, Gutstein W, Bartsch D U, et al. Visual function assessment in simulated real-life situations in patients with age-related macular degeneration compared to normal subjects. Eye (Lond). 2014; 28(10):1231-8.
3. Chiu S J, Izatt J A, O'Connell R V, Winter K P, Toth C A, Farsiu S. Validated automatic segmentation of AMD pathology including drusen and geographic atrophy in SD-OCT images. Invest Ophthalmol Vis Sci. 2012; 53(1): 53-61.
4. Hartong D T, Berson E L, Dryja T P. Retinitis pigmentosa. Lancet. 2006; 368(9549):1795-809.
5. Mezer E, Babul-Hirji R, Wise R, Chipman M, DaSilva L, Rowell M, et al. Attitudes Regarding Predictive Testing for Retinitis Pigmentosa. Ophthalmic Genetics. 2007; 28(1):9-15.
6. Chowers I, Banin E, Merin S, Cooper M, Granot E. Long-term assessment of combined vitamin A and E treatment for the prevention of retinal degeneration in abetalipoproteinaemia and hypobetalipoproteinaemia patients. Eye (Lond). 2001; 15 (Pt 4): 525-30.
7. Chong E W, Wong T Y, Kreis A J, Simpson J A, Guymer R H. Dietary antioxidants and primary prevention of age related macular degeneration: systematic review and meta-analysis. BMJ. 2007; 335(7623):755.
8. Klezovitch O, Risk M, Coleman I, Lucas J M, Null M, True L D, et al. A causal role for ERG in neoplastic transformation of prostate epithelium. Proc Natl Acad Sci USA. 2008; 105(6):2105-10.
9. Wildberger H, Niemeyer G, Junghardt A. Multifocal electroretinogram (mfERG) in a family with occult macular dystrophy (OMD). Klin Monbl Augenheilkd. 2003; 220(3):111-5.

10. Shimada Y, Li Y, Bearse M A, Jr., Sutter E E, Fung W. Assessment of early retinal changes in diabetes using a new multifocal ERG protocol. Br J Ophthalmol. 2001; 85(4):414-9.
11. Palmowski A M, Sutter E E, Bearse M A, Jr., Fung W. Mapping of retinal function in diabetic retinopathy using the multifocal electroretinogram. Invest Ophthalmol Vis Sci. 1997; 38(12):2586-96.
12. Waheed N K, Moult E M, Fujimoto J G, Rosenfeld P J. Optical Coherence Tomography Angiography of Dry Age-Related Macular Degeneration. Dev Ophthalmol. 2016; 56:91-100.
13. Hee M R, Puliafito C A, Wong C, Duker J S, Reichel E, Schuman J S, et al. Optical coherence tomography of macular holes. Ophthalmology. 1995; 102(5):748-56.
14. Hee M R, Izatt J A, Swanson E A, Huang D, Schuman J S, Lin C P, et al. Optical coherence tomography of the human retina. Arch Ophthalmol. 1995; 113(3):325-32.
15. Swanson E A, Izatt J A, Hee M R, Huang D, Lin C P, Schuman J S, et al. In vivo retinal imaging by optical coherence tomography. Opt Lett. 1993; 18(21):1864-6.
16. Chabrier C L L, Schnitzler J Y, Wassmer B. System and apparatus for providing ophthalmic images for diagnosis and treatment. United States patent application U.S. Ser. No. 14/758,721 2015. QUANTEL MEDICAL Inc.
17. Hacker M E R, Pabst T, Peterlein U, Antkowiak G, Bergner R, Koschmieder I. Device for swept-source optical coherence domain reflectometry. U.S. Pat. No. 8,690,330 2014 Apr. 8. Carl Zeiss Meditec AG.
18. Ramo J P P J, Ricart M V, CARBONELL M A, Garcia R B. Method for the detection of visual function losses. U.S. Pat. No. 9,750,406 2017 Universitat Politecnica de Catalunya.
19. Ramos J D dSVN, Santos F T, da Silva Pinto J P. Methods and systems for detection of retinal changes. U.S. Pat. No. 8,041,091 2011.
20. Mohanty S K, Ghosh N, Bhattacharya S, inventors; NanoScope Technologies, LLC, assignee. Cancer Diagnosis by Refractive Index Multifractality. U.S. patent 62/206,975. 2015.
21. Gu L, Mohanty S K. Targeted microinjection into cells and retina using optoporation. J Biomed Opt. 2011; 16(12):128003-6.
22. Mohanty S K, Reinscheid R K, Liu X, Okamura N, Krasieva T B, Berns M W. In-Depth Activation of Channelrhodopsin 2-Sensitized Excitable Cells with High Spatial Resolution Using Two-Photon Excitation with a Near-Infrared Laser Microbeam. Biophys J. 2008; 95(8):3916-26.
23. Zhang F, Wang L-P, Brauner M, Liewald J F, Kay K, Watzke N, et al. Multimodal fast optical interrogation of neural circuitry. Nature. 2007; 446(7136):633-9.
24. Wojtkowski M, Srinivasan V, Fujimoto J G, Ko T, Schuman J S, Kowalczyk A, et al. Three-dimensional retinal imaging with high-speed ultrahigh-resolution optical coherence tomography. Ophthalmology. 2005; 112 (10):1734-46.
25. Witkin A J, Ko T H, Fujimoto J G, Chan A, Drexler W, Schuman J S, et al. Ultra-high resolution optical coherence tomography assessment of photoreceptors in retinitis pigmentosa and related diseases. Am J Ophthalmol. 2006; 142(6):945-52.
26. B. E. Bouma aGJT. Handbook of Optical Coherence Tomography. New York: Informa Healthcare; 2001.
27. Brezinski M. Optical Coherence Tomography: Principles and Applications. London: Academic Press; 2006.
28. Fercher A F, Drexler W, Hitzenberger C K, Lasser T. Optical coherence tomography—principles and applications. Reports on Progress in Physics. 2003; 66(2):239.
29. Hausler G, Lindner M W. "Coherence Radar" and "Spectral Radar"—New Tools for Dermatological Diagnosis. Journal of Biomedical Optics. 1998; 3(1):21-31.
30. Tomlins P H, Wang R K. Theory, developments and applications of optical coherence tomography. Journal of Physics D: Applied Physics. 2005; 38(15):2519.
31. Zhao Y, Chen Z, Saxer C, Xiang S, de Boer J F, Nelson J S. Phase-resolved optical coherence tomography and optical Doppler tomography for imaging blood flow in human skin with fast scanning speed and high velocity sensitivity. Optics letters. 2000; 25(2):114-6.
32. Jia Y, Morrison J C, Tokayer J, Tan O, Lombardi L, Baumann B, et al. Quantitative OCT angiography of optic nerve head blood flow. Biomedical optics express. 2012; 3(12):3127-37.
33. Mukhopadhyay S, Das N K, Kurmi I, Pradhan A, Ghosh N, Panigrahi P K. Tissue multifractality and hidden Markov model based integrated framework for optimum precancer detection. J Biomed Opt. 2017; 22(10):1-8.
34. Terao T, Nakayama T, Aoki H. Multifractality of the quantum Hall wave functions in higher Landau levels. Phys Rev B Condens Matter. 1996; 54(15):10350-3.
35. Batabyal S, Satpathy S, Bui L, Kim Y T, Mohanty S, Bachoo R, et al. Label-free optical detection of action potential in mammalian neurons. Biomedical optics express. 2017; 8(8):3700-13.
36. Yeh Y J, Black A J, Akkin T. Spectral-domain low-coherence interferometry for phase-sensitive measurement of Faraday rotation at multiple depths. Appl Opt. 2013; 52(29):7165-70.
37. Akkin T, Dave D P, Milner T E, Rylander Iii H G. Detection of neural activity using phase-sensitive optical low-coherence reflectometry. Opt Express. 2004; 12(11): 2377-86.
38. Choma M A, Ellerbee A K, Yang C, Creazzo T L, Izatt J A. Spectral-domain phase microscopy. Opt Lett. 2005; 30(10):1162-4.
39. Grunwald J E, Pistilli M, Ying G S, Maguire M G, Daniel E, Martin D F. Growth of Geographic Atrophy in the Comparison of Age-related Macular Degeneration Treatments Trials. Ophthalmology. 2014.
40. Wu Z, Ayton L N, Luu C D, Guymer R H. Microperimetry of nascent geographic atrophy in age-related macular degeneration. Invest Ophthalmol Vis Sci. 2015; 56(1): 115-21.
41. Wallsh J, Gallemore R. Optical coherence tomography difference maps and average macular volume for geographic atrophy. Retin Cases Brief Rep. 2015; 9(1):88-91.
42. Biarnes M, Mones J, Alonso J, Arias L. Update on geographic atrophy in age-related macular degeneration. Optom Vis Sci. 2011; 88(7):881-9.
43. Sunness J S, Margalit E, Srikumaran D, Applegate C A, Tian Y, Perry D, et al. The long-term natural history of geographic atrophy from age-related macular degeneration: enlargement of atrophy and implications for interventional clinical trials. Ophthalmology. 2007; 114(2): 271-7.
44. Busskamp V, Picaud S, Sahel J A, Roska B. Optogenetic therapy for retinitis pigmentosa. Gene Ther. 2012; 19(2): 169-75.
45. Nagel G, Szellas T, Huhn W, Kateriya S, Adeishvili N, Berthold P, et al. Channelrhodopsin-2, a directly light-gated cation-selective membrane channel. Proc Nat Acad Sci. 2003; 100(24):13940-5.

46. Boyden E S, Zhang F, Bamberg E, Nagel G, Deisseroth K. Millisecond-timescale, genetically targeted optical control of neural activity. Nat Neurosci. 2005; 8(9):1263-8.
47. Miller G. Shining New Light on Neural Circuits. Science. 2006; 314(5806):1674-6.
48. Zhang F, Aravanis A M, Adamantidis A, de Lecea L, Deisseroth K. Circuit-breakers: optical technologies for probing neural signals and systems. Nat Rev Neurosci. 2007; 8(8):577-81.
49. Zhang F, Wang L P, Boyden E S, Deisseroth K. Channelrhodopsin-2 and optical control of excitable cells. Nat Methods. 2006; 3(10):785-92.
50. Zhang F, Aravanis A M, Adamantidis A, de Lecea L, Deisseroth K. Circuit-breakers: optical technologies for probing neural signals and systems. Nat Rev Neurosci. 2007; 8(8):577-81.
51. Sugawara T, Hagiwara A, Hiramatsu A, Ogata K, Mitamura Y, Yamamoto S. Relationship between peripheral visual field loss and vision-related quality of life in patients with retinitis pigmentosa. Eye (Lond). 2010; 24(4):535-9.
52. Daiger S P, Bowne S J, Sullivan L S. Perspective on genes and mutations causing retinitis pigmentosa. Arch Ophthalmol. 2007; 125(2):151-8.
53. Flannery J G, Farber D B, Bird A C, Bok D. Degenerative changes in a retina affected with autosomal dominant retinitis pigmentosa. Invest Ophthalmol Vis Sci. 1989; 30(2):191-211.
54. Hartong D T, Berson E L, Dryja T P. Retinitis pigmentosa. Lancet. 2006; 368(9549):1795-809.
55. Chader G J. Animal models in research on retinal degenerations: past progress and future hope. Vision Res. 2002; 42(4):393-9.
56. Li Z Y, Jacobson S G, Milam A H. Autosomal dominant retinitis pigmentosa caused by the threonine-17-methionine rhodopsin mutation: retinal histopathology and immunocytochemistry. Exp Eye Res. 1994; 58(4):397-408.
57. Grover S, Fishman G A, Anderson R J, Alexander K R, Derlacki D J. Rate of visual field loss in retinitis pigmentosa. Ophthalmology. 1997; 104(3):460-5.
58. Adler D C, Huber R, Fujimoto J G. Phase-sensitive optical coherence tomography at up to 370,000 lines per second using buffered Fourier domain mode-locked lasers. Opt Lett. 2007; 32(6):626-8.
59. Joo C, Kim K H, de Boer J F. Spectral-domain optical coherence phase and multiphoton microscopy. Opt Lett. 2007; 32(6):623-5.
60. Sarunic M V, Weinberg S, Izatt J A. Full-field swept-source phase microscopy. Opt Lett. 2006; 31(10):1462-4.
61. Wang R K, Nuttall A L. Phase-sensitive optical coherence tomography imaging of the tissue motion within the organ of Corti at a subnanometer scale: a preliminary study. Journal of Biomedical Optics. 2010; 15(5):056005-9.
62. Kim B J, Braun T A, Wordinger R J, Clark A F. Progressive morphological changes and impaired retinal function associated with temporal regulation of gene expression after retinal ischemia/reperfusion injury in mice. Mol Neurodegener. 2013; 8:21.

What is claimed is:

1. A contact-less, label-free optical device for near real time quantification of cellular activities of a retina of an eye in mammals comprising:
    a visual stimulation source configured to generate a stimulating beam;
    a low coherence or a swept light source configured to generate an optical probing beam;
    a fiber coupler configured to couple the stimulating beam and the optical probing beam to generate a light beam;
    a coupler configured to split the generated light beam into a reference beam and a sample beam;
    a fixed reference mirror configured to reflect the reference beam;
    at least one XY-scanning mirror configured to scan the sample beam that impinges on different layers of the retina;
    wherein a back-reflected sample signal of the sample beam is configured to interfere with a back-reflected reference signal of the reference beam to generate an interferometric signal;
    a detector configured to detect the interferometric signal; and
    a processing unit configured to process and analyze the interferometric signal.

2. The device of claim 1, wherein the interferometric signal is configured to be processed and analyzed to obtain at least one of time-dependent amplitude, phase and multifractality information from different layers,
    wherein at least one of amplitude and phase information is configured to be obtained from at least one position;
    wherein at least one of amplitude and phase information is configured to be collected in synchronization with visual stimulation,
    wherein the stimulation is configured to be applied simultaneously or sequentially at least at one point; and
    further comprising a tracking algorithm based on fundus images for compensating the eye movement between the phase measurements.

3. The device of claim 1, wherein the low coherence or the swept light source has a center which has a wavelength in the near infrared range from 700-1100 nm and the bandwidth of the light source up to 400 nm.

4. The device of claim 1, wherein the visual stimulation source is optical and it has a center which has a wavelength range from 400-700 nm, and the bandwidth of the light source ranges up to 300 nm.

5. The device of claim 1, wherein the device is configured as a handheld portable device consisting of a scanning head, the visual stimulation source for scanning visual stimulation, and computer hardware and software for scanning targeted retina layers and obtaining functional data.

6. The device of claim 1, wherein the sample beam is configured to obtain at least one of amplitude and phase information from different locations in the retina.

7. The device of claim 1, wherein the optical probing beam is generated by a low coherence light source and wherein the detector is a spectrometer.

8. The device of claim 1, wherein the optical probing beam is generated by a swept light source and wherein the detector is a photodiode or a camera.

9. A method for near real time quantification of cellular activities of a retina of an eye in mammals comprising:
    stimulating the eye with a visual stimulation source configured to generate a stimulating beam;
    providing at least one of a low coherence or a swept light source configured to generate an optical probing beam;
    coupling the stimulating beam and the optical probing beam by using a fiber coupler to generate a light beam;
    splitting the generated light beam by using a coupler into a reference beam and a sample beam;
    reflecting the reference beam with a fixed reference mirror, scanning the sample beam to impinge on different layers of the retina by using at least one XY-scanning mirror;

generating an interferometric signal by interfering a back-reflected sample signal of the sample beam and a back-reflected reference signal of the reference beam;

detecting the interferometric signal with a detector; and processing and analyzing the interferometric signal with a processing unit.

10. The method of claim 9, comprising generating at least one A-scan from different points of the interferometric signal to obtain a measurement of at least one of amplitude and optical path difference and changes of time varying multifractal parameters from amplitude or phase information.

11. The method of claim 9, comprising analyzing the interferometric signal by at least one of fast Fourier transform, envelope detection, rolling, moving averaging, and multifractal analysis to measure fluctuations in the layer of the retina.

12. The method of claim 9, comprising functionally characterizing retinal cells in mammals by obtaining the change in optical path difference and multifractal parameters comprising width of the singularity spectrum, Hurst exponent, fractal dimension, locally connected fractal mapping, and optical retinogram during at least one of focal and global visual stimulation of different light intensities and durations.

13. The method of claim 12, comprising the step of measuring the optical retinogram to provide a method for the diagnosis and monitoring the progression of retinal disease in a mammalian subject's eye.

14. The method of claim 12, comprising enhancing the optical retinogram signal by use of exogenous molecules, or gold nanostructures, functionalized to target specific retinal layers.

15. The method of claim 12, comprising the step of measuring the optical retinogram changes to provide information on individual retinal layer encoded in different frequencies of optical interferogram and to provide information on physiochemical changes upon visual stimulation.

16. The method of claim 12, comprising the step of measuring the optical retinogram signal to provide data for healthy retinal activity upon visual stimulation and the data is used as a reference standard to make a medical decision about at least one of the disease state and grading of the disease state by developing hybrid screening algorithm using ffORG data driven artificial intelligence comprising at least one of basic machine learning, advanced machine learning, hidden Markov modeling, and deep learning with convolutional neural network.

17. The method of claim 12, comprising measuring a positive or negative amplitude, a latency of a positive or negative peak, and a rate of decay or growth of a temporal profile, and multifractal parameters of the optical retinogram signal from the optical signal to determine the retinal cell types responsible for the functional outcome and monitor their activity for pharmacological and/or physical intervention comprising biomodulation using light, electrical, magnetic, acoustic or thermal means, wherein layer-specific activity measurements are obtained by low coherence optical interferometry in combination with visual stimulation;

wherein a larger increase in optical path difference in response to visual stimulation is attributed to photoreceptors;

wherein fluctuations and/or rate of decay or growth of the temporal profile of the optical path difference signal is used to determine cell types and response characteristics of endogenous and exogenous opsins or molecules;

wherein latency of peak of change in optical path difference profile in response to visual stimulation determines the retinal cell type in a visual transduction pathway responsible for the measured activities;

wherein the retinal cell type and its functional state is identified from the amplitude of positive or negative peak of the temporal profile of the measured optical path difference; and wherein the multifractal parameter(s) calculated from the measured Optical RetinoGram signal delineates the functioning cell types and disease detection.

18. The method of claim 12, comprising the step of obtaining positive or negative amplitudes of the temporal profiles of the optical retinogram signals with stimulation of light of different wavelengths and bandwidths to obtain photosensitive function and activation spectrum of the measured retinal region(s) or cell(s), wherein the photosensitive function and activation spectrum is a plot of the variation of amplitude of the optical retinogram signal as a function of the wavelength of the stimulating light.

19. The method of claim 12, comprising the step of registering image sequences and comprising the step of analyzing the optical retinogram signal to extract phase fluctuation rate, multifractal parameters and characteristics in an individual layer of the retina in response to single or multiple pulses or continuous stimulation by at least one of light, electrical, magnetic, acoustic, and thermal energy, wherein the phase fluctuation rate is quantified by standard deviation and multifractal parameters; and wherein the multifractal parameters are fractal dimension, and width of a singularity spectrum.

20. The method of claim 12, comprising the step of screening or optimizing one or more therapeutic drugs, devices, protocols, and/or comprising the step of monitoring recovery of retinal function due to therapeutic treatment by at least one of gene therapy, cell therapy and regenerative medicine.

21. The method of claim 12, comprising the step of applying a tracking algorithm to position at least one of the stimulating or optical probing beam to the desired area(s) of the retina to compensate for eye movements.

* * * * *